US011179437B2

(12) United States Patent
Sharon et al.

(10) Patent No.: US 11,179,437 B2
(45) Date of Patent: Nov. 23, 2021

(54) COP9 SIGNALOSOME (CSN) COMPLEX MODULATORS AND USES THEREOF

(71) Applicant: Yeda Research and Development Co. Ltd., Rehovot (IL)

(72) Inventors: Michal Sharon, Rehovot (IL); Maria Gabriella Fuzesi-Levi, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 16/899,647

(22) Filed: Jun. 12, 2020

(65) Prior Publication Data

US 2020/0297796 A1    Sep. 24, 2020

Related U.S. Application Data

(63) Continuation of application No. PCT/IL2018/051365, filed on Dec. 17, 2018.

(60) Provisional application No. 62/599,721, filed on Dec. 17, 2017.

(51) Int. Cl.
*A61K 38/10* (2006.01)
*C12N 15/113* (2010.01)

(52) U.S. Cl.
CPC .......... *A61K 38/10* (2013.01); *C12N 15/1136* (2013.01)

(58) Field of Classification Search
None
See application file for complete search history.

(56) References Cited

U.S. PATENT DOCUMENTS

| | | | | |
|---|---|---|---|---|
| 7,947,672 B2* | 5/2011 | Scherz | ............... | A61K 41/0076 |
| | | | | 514/184 |
| 8,461,142 B2* | 6/2013 | Scherz | .................... | A61P 31/00 |
| | | | | 514/185 |
| 9,764,008 B2* | 9/2017 | Sagi | ........................ | A61P 29/00 |
| 10,336,789 B2* | 7/2019 | Oren | ........................ | A61P 1/04 |
| 10,369,172 B2* | 8/2019 | Reisner | ................... | A61K 35/36 |
| 10,434,121 B2* | 10/2019 | Reisner | ................... | A61K 35/36 |
| 10,550,152 B2* | 2/2020 | Oren | ........................ | C07K 7/08 |
| 2003/0153097 A1 | 8/2003 | Deshaies et al. | | |
| 2016/0219910 A1* | 8/2016 | Silver | .................. | A61K 9/2054 |
| 2016/0228506 A1* | 8/2016 | Afeyan | ................... | A23L 33/18 |
| 2019/0091300 A1* | 3/2019 | Teichberg | ............ | A61K 31/194 |
| 2019/0125769 A1* | 5/2019 | Scherz | .................... | A61P 35/00 |
| 2019/0314312 A1* | 10/2019 | Erez | ....................... | A61K 31/366 |
| 2019/0328793 A1* | 10/2019 | Reisner | ................... | A61K 35/38 |
| 2019/0343934 A1* | 11/2019 | Sagi | ........................ | A61P 29/00 |
| 2019/0358269 A1* | 11/2019 | Reisner | ................ | A61K 31/675 |
| 2020/0094069 A1* | 3/2020 | Scherz | .................... | A61P 35/04 |
| 2020/0095282 A1* | 3/2020 | Oren | ...................... | A61K 38/08 |
| 2020/0362018 A1* | 11/2020 | Sharon | ............... | C07K 14/8107 |

FOREIGN PATENT DOCUMENTS

| | | |
|---|---|---|
| WO | WO 2015/048340 | 4/2015 |
| WO | WO 2019/116376 | 6/2019 |
| WO | WO 2019/116376 A9 | 6/2019 |

OTHER PUBLICATIONS

Partial sequence listing for US 20160219910.*
Yampolsky, Lev Y. and Stoltzfus, Arlin; "The exchangeability of amino acids in proteins." Genetics (2005) 170 p. 1459-1472.*
Sequence listing for US 201600228506.*
International Preliminary Report on Patentability dated Jul. 2, 2020 From the International Bureau of WIPO Re. Application No. PCT/IL2018/051365. (12 Pages).
International Search Report and the Written Opinion dated Apr. 8, 2019 From the International Searching Authority Re. Application No. PCT/IL2018/051365. (20 Pages).
Barth et al. "The Evolution of COP9 Signalosome in Unicellular and Multicellular Organisms", Genome Biology and Evolution, XP055564660, 8(4): 1279-1289, Advance Access Publication Apr. 4, 2016.
Fuzesi-Levi et al. "The Essentiality of CSNAP for CSN Function", The FEBS Journal, XP055564791, Posters, 284(Suppl.1): 142, # P.1.5-067, Sep. 11, 2017.
Füzesi-Levi et al. "CSNAP, The Novel COP9 Signalosome Subunit, Coordinates Interactions With CRLs", Poster, FEBS Meeting, Jerusalem, Israel, Sep. 2017.
Rozen et al. "CSNAP Is a Stoichiometric Subunit of the COP9 Signalosome", Cell Reports, XP055564657, 13(3): 585-598, Oct. 20, 2015.

* cited by examiner

*Primary Examiner* — Fred H Reynolds

(57) ABSTRACT

A method of treating a condition associated with aberrant protein degradation is disclosed. The method comprises administering to a subject in need thereof a therapeutically effective amount of an agent, which reduces the amount of CSN Acidic Protein (CSNAP) which is incorporated into the COP9 signalosome complex (CSN) of the cell.

Figure 1A:
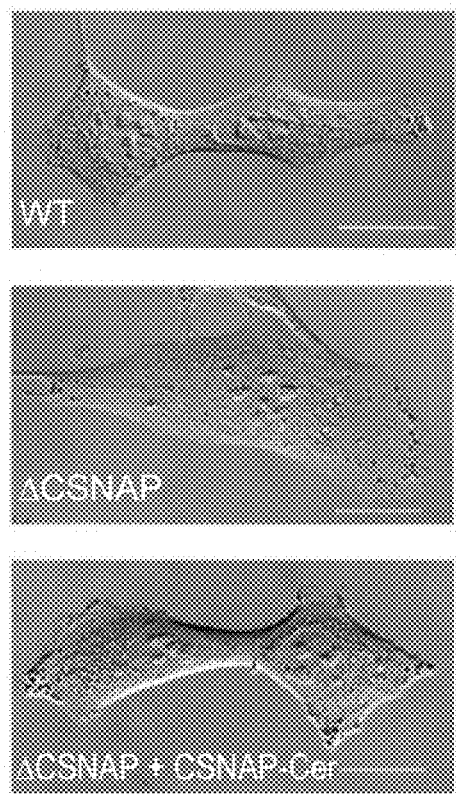

1 Claim, 12 Drawing Sheets
(8 of 12 Drawing Sheet(s) Filed in Color)
Specification includes a Sequence Listing.

FIG. 3B
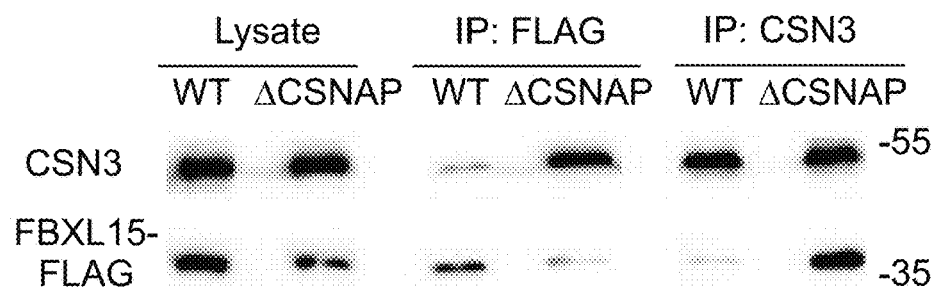
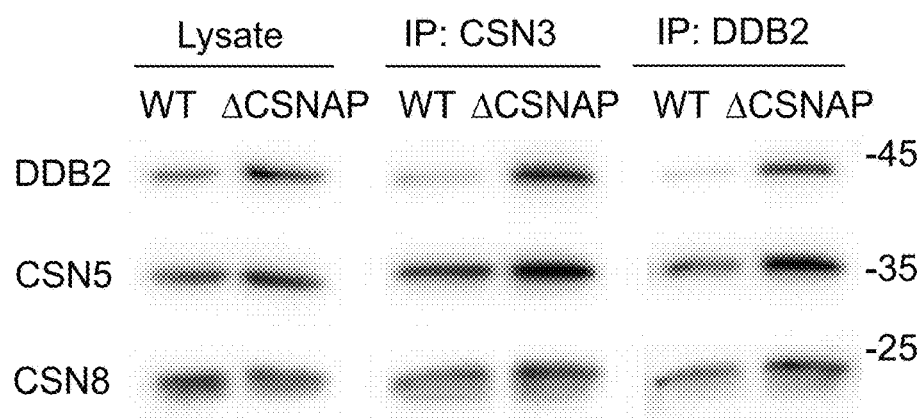
FIG. 3C
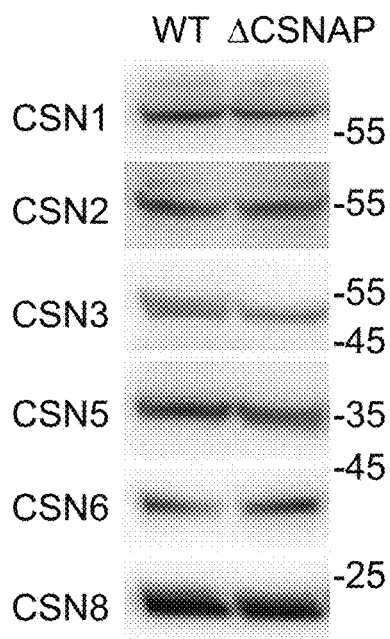
FIG. 3D
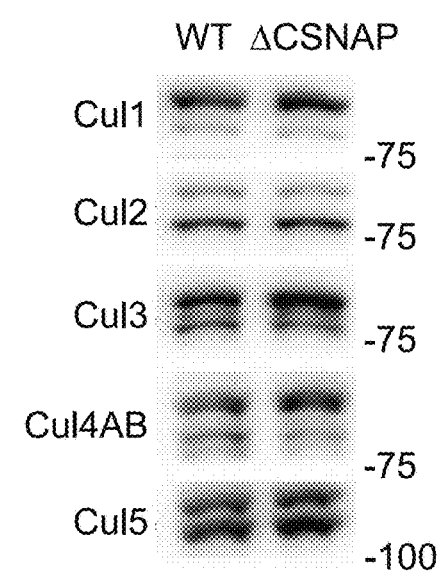

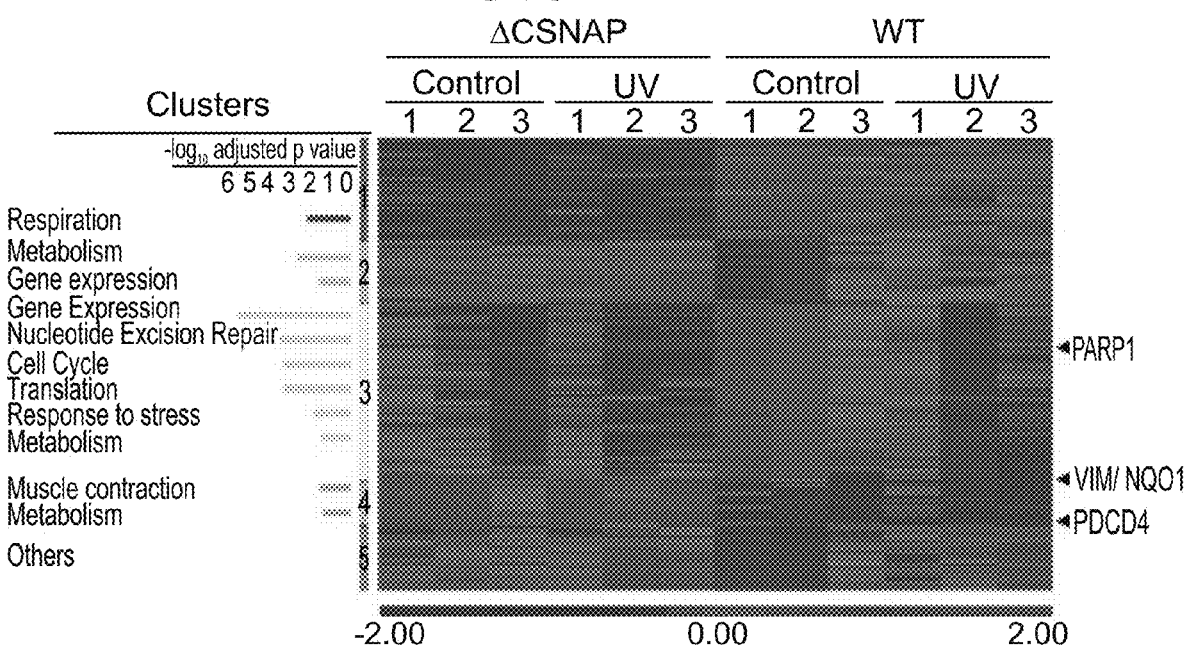
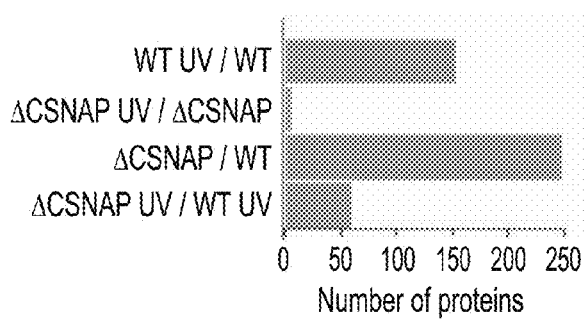
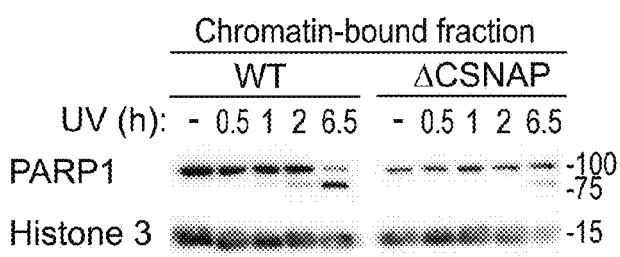
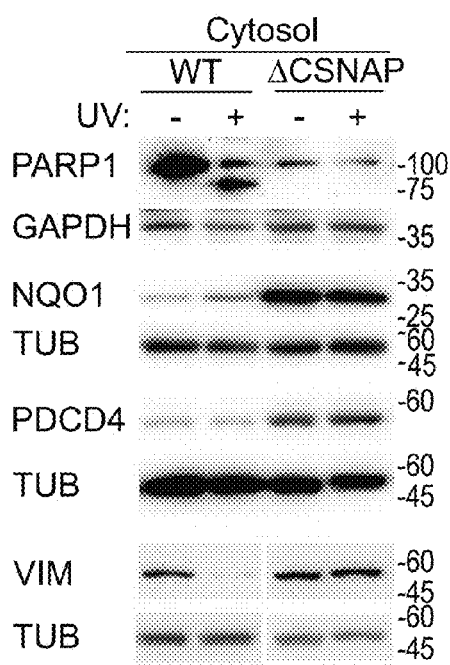

FIG. 10

SEQUENCE LISTING

<160> NUMBER OF SEQ ID NOS: 35

<210> SEQ ID NO 1
<211> LENGTH: 16
<212> TYPE: PRT
<213> ORGANISM: Artificial sequence
<220> FEATURE:
<223> OTHER INFORMATION: C-terminal segment of CSNAP

<400> SEQUENCE: 1

Asp Phe Phe Asn Asp Phe Glu Asp Leu Phe Asp Asp Asp Ile Gln
1               5                   10                  15

<210> SEQ ID NO 2
<211> LENGTH: 57
<212> TYPE: PRT
<213> ORGANISM: Homo sapiens

<400> SEQUENCE: 2

Met Lys Pro Ala Val Asp Glu Met Phe Pro Glu Gly Ala Gly Pro Tyr
1               5                   10                  15

Val Asp Leu Asp Glu Ala Gly Gly Ser Thr Gly Leu Leu Met Asp Leu
            20                  25                  30

Ala Ala Asn Glu Lys Ala Val His Ala Asp Phe Phe Asn Asp Phe Glu
            35                  40                  45

Asp Leu Phe Asp Asp Asp Ile Gln
    50                  55

<210> SEQ ID NO 3
<211> LENGTH: 7
<212> TYPE: PRT
<213> ORGANISM: Artificial sequence
<220> FEATURE:
<223> OTHER INFORMATION: Examples of peptide penetrating agent

<400> SEQUENCE: 3

Tyr Gly Arg Lys Lys Arg Arg
1               5

<210> SEQ ID NO 4
<211> LENGTH: 11
<212> TYPE: PRT
<213> ORGANISM: Artificial sequence
<220> FEATURE:
<223> OTHER INFORMATION: Examples of peptide penetrating agent

<400> SEQUENCE: 4

Tyr Gly Arg Lys Lys Arg Arg Gln Arg Arg Arg
1               5                   10

<210> SEQ ID NO 5
<211> LENGTH: 5
<212> TYPE: PRT
<213> ORGANISM: Artificial sequence
<220> FEATURE:
<223> OTHER INFORMATION: Examples of peptide penetrating agent

<400> SEQUENCE: 5

Arg Arg Gln Arg Arg
1               5

<210> SEQ ID NO 6
<211> LENGTH: 41
<212> TYPE: PRT
<213> ORGANISM: Artificial sequence
<220> FEATURE:
<223> OTHER INFORMATION: truncated CSNAP

<400> SEQUENCE: 6

Met Lys Pro Ala Val Asp Glu Met Phe Pro Glu Gly Ala Gly Pro Tyr
1               5                   10                  15

Val Asp Leu Asp Glu Ala Gly Gly Ser Thr Gly Leu Leu Met Asp Leu
            20                  25                  30

Ala Ala Asn Glu Lys Ala Val His Ala
            35                  40

<210> SEQ ID NO 7
<211> LENGTH: 13
<212> TYPE: PRT
<213> ORGANISM: Artificial sequence
<220> FEATURE:
<223> OTHER INFORMATION: cell penetrating peptide (CPP) sequence

<400> SEQUENCE: 7

Gly Arg Lys Lys Arg Arg Gln Arg Arg Arg Pro Pro Gln
1               5                   10

<210> SEQ ID NO 8

```
<211> LENGTH: 12
<212> TYPE: PRT
<213> ORGANISM: Artificial sequence
<220> FEATURE:
<223> OTHER INFORMATION: cell penetrating peptide (CPP) sequence

<400> SEQUENCE: 8

Gly Arg Lys Lys Arg Arg Gln Arg Arg Arg Pro Pro
1               5                   10

<210> SEQ ID NO 9
<211> LENGTH: 11
<212> TYPE: PRT
<213> ORGANISM: Artificial sequence
<220> FEATURE:
<223> OTHER INFORMATION: cell penetrating peptide (CPP) sequence

<400> SEQUENCE: 9

Gly Arg Lys Lys Arg Arg Gln Arg Arg Arg Pro
1               5                   10

<210> SEQ ID NO 10
<211> LENGTH: 10
<212> TYPE: PRT
<213> ORGANISM: Artificial sequence
<220> FEATURE:
<223> OTHER INFORMATION: cell penetrating peptide (CPP) sequence

<400> SEQUENCE: 10

Gly Arg Lys Lys Arg Arg Gln Arg Arg Arg
1               5                   10

<210> SEQ ID NO 11
<211> LENGTH: 9
<212> TYPE: PRT
<213> ORGANISM: Artificial sequence
<220> FEATURE:
<223> OTHER INFORMATION: cell penetrating peptide (CPP) sequence

<400> SEQUENCE: 11

Gly Arg Lys Lys Arg Arg Gln Arg Arg
1               5

<210> SEQ ID NO 12
<211> LENGTH: 8
<212> TYPE: PRT
<213> ORGANISM: Artificial sequence
<220> FEATURE:
<223> OTHER INFORMATION: cell penetrating peptide (CPP) sequence

<400> SEQUENCE: 12

Gly Arg Lys Lys Arg Arg Gln Arg
1               5

<210> SEQ ID NO 13
<211> LENGTH: 7
<212> TYPE: PRT
<213> ORGANISM: Artificial sequence
<220> FEATURE:
<223> OTHER INFORMATION: cell penetrating peptide (CPP) sequence

<400> SEQUENCE: 13

Gly Arg Lys Lys Arg Arg Gln
1               5

<210> SEQ ID NO 14
<211> LENGTH: 7
```

-continued

```
<212> TYPE: PRT
<213> ORGANISM: Artificial sequence
<220> FEATURE:
<223> OTHER INFORMATION: cell penetrating peptide (CPP) sequence

<400> SEQUENCE: 14

Tyr Gly Arg Lys Lys Arg Arg
1               5

<210> SEQ ID NO 15
<211> LENGTH: 11
<212> TYPE: PRT
<213> ORGANISM: Artificial sequence
<220> FEATURE:
<223> OTHER INFORMATION: cell penetrating peptide (CPP) sequence

<400> SEQUENCE: 15

Tyr Gly Arg Lys Lys Arg Arg Gln Arg Arg
1               5                   10

<210> SEQ ID NO 16
<211> LENGTH: 5
<212> TYPE: PRT
<213> ORGANISM: Artificial sequence
<220> FEATURE:
<223> OTHER INFORMATION: cell penetrating peptide (CPP) sequence

<400> SEQUENCE: 16

Arg Arg Gln Arg Arg
1               5

<210> SEQ ID NO 17
<211> LENGTH: 9
<212> TYPE: RNA
<213> ORGANISM: Artificial sequence
<220> FEATURE:
<223> OTHER INFORMATION: Examples of oligonucleotide sequences that can
      be used to form the shRNA loop

<400> SEQUENCE: 17 uucaagaga                                                                9

<210> SEQ ID NO 18
<211> LENGTH: 9
<212> TYPE: RNA
<213> ORGANISM: Artificial sequence
<220> FEATURE:
<223> OTHER INFORMATION: Examples of oligonucleotide sequences that can
      be used to form the shRNA loop

<400> SEQUENCE: 18 uuuguguag                                                                9

<210> SEQ ID NO 19
<211> LENGTH: 57
<212> TYPE: PRT
<213> ORGANISM: Homo sapiens

<400> SEQUENCE: 19

Met Lys Pro Ala Val Asp Glu Met Phe Pro Glu Gly Ala Gly Pro Tyr
1               5                   10                  15

Val Asp Leu Asp Glu Ala Gly Gly Ser Thr Gly Leu Leu Met Asp Leu
                20                  25                  30

Ala Ala Asn Glu Lys Ala Val His Ala Asp Phe Phe Asn Asp Phe Glu
            35                  40                  45
```

```
Asp Leu Phe Asp Asp Asp Ile Gln
        50                  55

<210> SEQ ID NO 20
<211> LENGTH: 57
<212> TYPE: PRT
<213> ORGANISM: Bos Taurus

<400> SEQUENCE: 20

Met Lys Pro Ala Val Asp Glu Met Phe Pro Glu Gly Ala Gly Pro Tyr
1               5                   10                  15

Val Asp Leu Asp Glu Ala Gly Gly Ser Thr Gly Leu Leu Met Asp Leu
                20                  25                  30

Ala Ala Asn Glu Lys Ala Val His Ala Asp Phe Phe Asn Asp Phe Glu
            35                  40                  45

Asp Leu Phe Asp Asp Asp Ile Gln
        50                  55

<210> SEQ ID NO 21
<211> LENGTH: 57
<212> TYPE: PRT
<213> ORGANISM: Mus musculus

<400> SEQUENCE: 21

Met Lys Pro Ala Val Asp Glu Met Phe Pro Glu Gly Ala Gly Pro Tyr
1               5                   10                  15

Val Asp Leu Asp Glu Ala Gly Gly Ser Thr Gly Leu Leu Met Asp Leu
                20                  25                  30

Ala Ala Asn Glu Lys Ala Val His Ala Asp Phe Phe Asn Asp Phe Glu
            35                  40                  45

Asp Leu Phe Asp Asp Asp Val Gln
        50                  55

<210> SEQ ID NO 22
<211> LENGTH: 57
<212> TYPE: PRT
<213> ORGANISM: Gallus gallus

<400> SEQUENCE: 22

Met Lys Pro Ala Val Asp Glu Met Phe Pro Glu Gly Ala Gly Pro Tyr
1               5                   10                  15

Val Asp Leu Asp Glu Ala Gly Gly Ser Thr Gly Leu Leu Met Asp Leu
                20                  25                  30

Ala Ala Asn Glu Lys Ala Val His Ala Asp Phe Phe Asn Asp Phe Glu
            35                  40                  45

Asp Leu Phe Asp Asp Asp Ile Gln
        50                  55

<210> SEQ ID NO 23
<211> LENGTH: 57
<212> TYPE: PRT
<213> ORGANISM: Xenopus tropicalis

<400> SEQUENCE: 23

Met Lys Pro Ala Val Asp Glu Met Phe Pro Glu Gly Ala Gly Pro Tyr
1               5                   10                  15

Val Asp Leu Asp Glu Ala Gly Gly Ser Thr Gly Leu Leu Met Asp Leu
                20                  25                  30

Ala Ala Asn Glu Lys Ala Val His Ala Asp Phe Phe Asn Asp Phe Glu
            35                  40                  45
```

Asp Leu Phe Asp Asp Glu Asp Ile Gln
        50                  55

<210> SEQ ID NO 24
<211> LENGTH: 57
<212> TYPE: PRT
<213> ORGANISM: Danio rerio

<400> SEQUENCE: 24

Met Lys Pro Ala Val Asp Glu Met Phe Pro Glu Gly Ala Gly Pro Tyr
1               5                   10                  15

Val Asp Leu Asp Glu Ala Gly Gly Ser Ser Gly Leu Leu Met Asp Leu
            20                  25                  30

Ala Ala Asn Glu Lys Ala Val His Ser Asp Phe Phe Asn Asp Phe Glu
        35                  40                  45

Asp Leu Phe Asp Asp Asp Ile Gln
        50                  55

<210> SEQ ID NO 25
<211> LENGTH: 57
<212> TYPE: PRT
<213> ORGANISM: Callorhinchus milii

<400> SEQUENCE: 25

Met Lys Pro Ala Val Asp Glu Met Phe Pro Glu Gly Ala Gly Pro Tyr
1               5                   10                  15

Val Asp Leu Asp Glu Ala Gly Gly Ser Ser Gly Leu Leu Met Asp Leu
            20                  25                  30

Ala Ala Asn Glu Lys Ala Val His Ala Asp Phe Phe Asn Asp Phe Glu
        35                  40                  45

Asp Leu Phe Asp Asp Asp Ile Gln
        50                  55

<210> SEQ ID NO 26
<211> LENGTH: 57
<212> TYPE: PRT
<213> ORGANISM: Latimeria chalumnae

<400> SEQUENCE: 26

Met Lys Pro Ala Val Asp Glu Met Phe Pro Glu Gly Ala Gly Pro Tyr
1               5                   10                  15

Val Asp Leu Asp Glu Ala Gly Gly Ser Ser Gly Leu Leu Met Asp Leu
            20                  25                  30

Ala Ala Asn Glu Lys Ala Val His Ala Asp Phe Phe Asn Asp Phe Glu
        35                  40                  45

Asp Leu Phe Asp Asp Asp Ile Gln
        50                  55

<210> SEQ ID NO 27
<211> LENGTH: 62
<212> TYPE: PRT
<213> ORGANISM: Branchiostoma floridae

<400> SEQUENCE: 27

Met Lys Lys Met Lys Pro Ala Val Val Ala Asp Glu Met Phe Pro Glu
1               5                   10                  15

Gly Ala Gly Ser Phe Met Asp Leu Glu Glu Ala Gly Gly Ser Gly Gly
            20                  25                  30

Leu Met Met Glu Leu Ala Ala Asn Glu Lys Ala Val His Ser Asp Phe

-continued

```
                35                  40                  45

Phe Asn Asp Phe Asp Asp Leu Phe Asp Glu Asp Leu Ser
        50                  55                  60

<210> SEQ ID NO 28
<211> LENGTH: 60
<212> TYPE: PRT
<213> ORGANISM: Ciona intestinalis

<400> SEQUENCE: 28

Met Lys Pro Asn Thr Val Val Ala Asp Glu Met Phe Pro Asp Gly Ala
1               5                  10                  15

Tyr Asp Gly Asp Glu Ala Ser Val Gly Thr Ser Ser Val Gln Met
            20                  25                  30

Met Asp Ile Ser Ser Asn Glu Lys Ala Val His Ala Asp Phe Tyr Asn
        35                  40                  45

Asn Phe Glu Asp Leu Phe Asp Asp Gly Asp Leu Ser
    50                  55                  60

<210> SEQ ID NO 29
<211> LENGTH: 58
<212> TYPE: PRT
<213> ORGANISM: Strongylocentrotus purpuratus

<400> SEQUENCE: 29

Met Lys Pro Val Ala Val Asp Glu Met Phe Pro Glu Gly Ser Gly Pro
1               5                  10                  15

Tyr Val Asp Leu Asp Glu Ala Gly Gly Thr Ala Gly Leu Leu Met Asp
            20                  25                  30

Leu Ala Ala Asn Glu Lys Ala Val His Ser Asp Phe Phe Asn Asp Phe
        35                  40                  45

Asp Asp Leu Phe Asp Asp Glu Asp Leu Ser
    50                  55

<210> SEQ ID NO 30
<211> LENGTH: 71
<212> TYPE: PRT
<213> ORGANISM: Drosophila melanogaster

<400> SEQUENCE: 30

Met Asp Leu Asn Met Lys Pro Ser Leu Ala Asp Glu Met Phe Ser
1               5                  10                  15

Glu Gly Pro Gly Tyr Met Glu Met Asp Glu Ser Gly Gly Ala Thr Gly
            20                  25                  30

Met Met Met Asp His Leu Pro Ser Asn Asp Lys His Val His Ala Asp
        35                  40                  45

Phe Tyr Asn Asp Phe Asp Asp Leu Phe Asp Glu Asp Asn Trp Ala Lys
    50                  55                  60

Met Lys Thr Asp Gly Lys Gln
65                  70

<210> SEQ ID NO 31
<211> LENGTH: 60
<212> TYPE: PRT
<213> ORGANISM: Pandinus cavimanus

<400> SEQUENCE: 31

Met Lys Pro Gly Thr Val Val Ala Asp Glu Met Leu Pro Glu Gly Ala
1               5                  10                  15
```

Gly Pro Tyr Met Asp Leu Asp Glu Ala Gly Ser Gly Leu Leu
            20                  25                  30

Met Asp Leu Ala Ala Asn Glu Lys Ser Val His Ala Asp Phe Phe Asn
            35                  40                  45

Asp Phe Asp Asp Leu Phe Asp Asp Glu Asp Leu Gln
    50                  55                  60

<210> SEQ ID NO 32
<211> LENGTH: 59
<212> TYPE: PRT
<213> ORGANISM: Glycera tridactyla

<400> SEQUENCE: 32

Met Lys Pro Ser Leu Val Ala Asp Glu Met Phe Pro Glu Gly Ala Gly
1               5                   10                  15

Pro Tyr Met Asp Ile Glu Asp Ala Gly Gly Ser Ser Ala Leu Leu Met
            20                  25                  30

Asp Leu Ala Ala Asn Glu Lys Ser Val His Gly Glu Phe Tyr Asn Asp
            35                  40                  45

Phe Asp Asp Leu Phe Asp Asp Glu Asp Leu Ser
    50                  55

<210> SEQ ID NO 33
<211> LENGTH: 59
<212> TYPE: PRT
<213> ORGANISM: Lottia gigantea

<400> SEQUENCE: 33

Met Lys Pro Ala Ile Val Ala Asp Glu Met Phe Pro Glu Gly Ala Gly
1               5                   10                  15

Pro Tyr Met Asp Ile Glu Glu Ala Gly Gly Ser Ser Ala Leu Leu Met
            20                  25                  30

Asp Leu Ala Ala Asn Glu Lys Ser Val His Ser Asp Phe Phe Asn Asp
            35                  40                  45

Phe Glu Asp Leu Phe Asp Asp Glu Asp Leu Asn
    50                  55

<210> SEQ ID NO 34
<211> LENGTH: 60
<212> TYPE: PRT
<213> ORGANISM: Crassostrea gigas

<400> SEQUENCE: 34

Met Lys Pro Ala Ala Ile Val Ala Asp Glu Met Phe Pro Glu Gly Ala
1               5                   10                  15

Gly Pro Tyr Met Asp Ile Glu Glu Ala Gly Gly Ser Ser Ala Leu Leu
            20                  25                  30

Met Asp Leu Ala Ala Asn Glu Lys Ser Val His Ser Asp Phe Phe Asn
            35                  40                  45

Glu Phe Glu Asp Leu Phe Asp Asp Glu Asp Leu Ser
    50                  55                  60

<210> SEQ ID NO 35
<211> LENGTH: 62
<212> TYPE: PRT
<213> ORGANISM: Arabidopsis thaliana

<400> SEQUENCE: 35

Met Arg Pro Met Gln Leu Asp Met Leu Ser Glu Met Asp Asp Ala Gly
1               5                   10                  15

-continued

```
Ser Ser Met Ala Met Asp Val Asp Asp Leu Glu Ala Met Glu Ile Leu
            20                  25                  30

Asn Glu Gly Gly Leu Val Ser Asp Asn Lys Leu Ala Asp Ala Asp Phe
        35                  40                  45

Phe Asn Lys Phe Asp Asp Asp Phe Asp Asp Thr Asp Ile Asn
50                  55                  60
```

COP9 SIGNALOSOME (CSN) COMPLEX MODULATORS AND USES THEREOF

RELATED APPLICATIONS

This application is a Continuation of PCT Patent Application No. PCT/IL2018/051365 having international filing date of Dec. 17, 2018, which claims the benefit of priority under 35 USC § 119(e) of U.S. Provisional Patent Application No. 62/599,721 filed on Dec. 17, 2017. The contents of the above applications are all incorporated by reference as if fully set forth herein in their entirety.

SEQUENCE LISTING STATEMENT

The ASCII file, entitled 82960SequenceListing.txt, created on Jun. 12, 2020, comprising 14,756 bytes, submitted concurrently with the filing of this application is incorporated herein by reference.

FIELD AND BACKGROUND OF THE INVENTION

The present invention, in some embodiments thereof, relates to agents that regulate the COP9 signalosome (CSN) complex, more particularly, but not exclusively, to agents that reduce the incorporation of CSNAP into the CSN complex.

The evolutionarily conserved COP9 signalosome (CSN) complex is a key regulator of the ubiquitin-proteasome degradation pathway. In particular, the CSN controls the ubiquitination mechanism, a multistep process driven by the sequential action of three enzymes: E1 (ubiquitin-activating), E2 (ubiquitin-conjugating) and E3 (ubiquitin ligase). The resulting mono- or poly-ubiquitination events commonly trigger proteasome-mediated degradation of the substrates or initiate regulatory events. The CSN complex coordinates the specificity-generating step by controlling the activity of one of the major families of E3 ubiquitin ligases, the cullin-RING ligases (CRLs).

The CRL family constitutes about a third of all E3s in humans, mediating the ubiquitination of ~20% of the proteins degraded by the proteasome. Among them are many prominent cancer associated proteins such as p27, p53, MDM2, Smad7, Runx3, cyclinE, notch, β-catenin, smad, Id1, Skp2 and HIF1. CRLs are impressively diverse due to their combinatorial structure forming more than 250 distinct CRL modules, all of which are regulated by the CSN complex by means of two independent mechanisms: i) an enzymatic process involving deconjugation of the ubiquitin-like protein Nedd8 from the cullin subunit (deneddylation); and ii) physical binding to deneddylated CRLs, precluding interactions with E2 enzymes and ubiquitination substrates. The rigorous control of CRLs by the CSN is critical for an organism's normal development and survival and impairment of CSN function is linked with multiple cancers.

For many years, it had been thought that the CSN comprises eight canonical components known as CSN1 through CSN8, by descending order of molecular weights. However, an additional integral and stoichiometric subunit was recently identified. This subunit was named CSNAP, for CSN Acidic Protein (Rozen et al, Cell Reports, 2015). This subunit was found to be only 6.2 kDa, less than 2% of the total mass of the intact CSN complex (Rozen et al, Cell Rep 13, pages 585-598, 2015).

Additional background art includes US Patent Application No. 20030153097.

SUMMARY OF THE INVENTION

According to an aspect of the present invention there is provided a method of treating a condition associated with aberrant protein degradation, comprising administering to a subject in need thereof a therapeutically effective amount of an agent which reduces the amount of CSN Acidic Protein (CSNAP) which is incorporated into the COP9 signalosome complex (CSN) of the cell, thereby treating the condition associated with aberrant protein degradation.

According to an aspect of the present invention there is provided a method of treating a condition associated with aberrant protein degradation, comprising administering to a subject in need thereof a therapeutically effective amount of a peptide comprising an amino acid sequence of the C-terminus of CSNAP, thereby treating the condition associated with aberrant protein degradation.

According to an aspect of the present invention there is provided a composition of matter, which reduces the amount of CSN Acidic Protein (CSNAP) which is incorporated into the COP9 signalosome complex (CSN) of the cell.

According to an aspect of the present invention there is provided a pharmaceutical composition comprising as the active agent the composition of matter described herein and a pharmaceutically acceptable carrier.

According to an aspect of the present invention there is provided a method of screening for an agent which is useful for treating a condition associated with aberrant protein degradation, the method comprising:

(a) introducing the agent into a cell;
(b) analyzing the amount of CSNAP that is incorporated into the CSN of the cell, wherein a reduction in the amount of CSNAP that is incorporated into the CSN following step (a) is indicative that the agent is useful for treating condition associated with aberrant protein degradation.

According to embodiments of the present invention, the condition is a cell proliferative disorder, an inflammatory condition, or an autoimmune disorder.

According to embodiments of the present invention, the cell proliferative disorder is cancer or psoriasis.

According to embodiments of the present invention, the inflammatory disorder is an acute infection or a chronic inflammatory disorder.

According to embodiments of the present invention, the autoimmune disorder is multiple sclerosis or rheumatoid arthritis.

According to embodiments of the present invention, the condition is angiogenesis, asthma or ischemia and reperfusion injury.

According to embodiments of the present invention, the agent blocks the binding of said CSNAP to said COPS signalosome complex (CSN).

According to embodiments of the present invention, the agent blocks the binding of said CSNAP to the Csn3 or Csn5/6 subunit of said CSNAP.

According to embodiments of the present invention, the agent blocks the binding of said CSNAP to the Csn3 subunit of said CSNAP.

According to embodiments of the present invention, the agent is a peptide.

According to embodiments of the present invention, the peptide comprises an amino acid sequence of the C-terminus of CSNAP.

According to embodiments of the present invention, the amino acid sequence is as set forth in SEQ ID NO: 1.

According to embodiments of the present invention, the amino acid sequence of the C-terminus of CSNAP is no longer than 30 amino acids.

According to embodiments of the present invention, the agent is attached to a cell penetrating moiety.

According to embodiments of the present invention, the peptide is devoid of the N-terminal sequence of CSNAP.

According to embodiments of the present invention, the agent is a polynucleotide agent directed against a polynucleotide encoding CSNAP.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-E illustrate that the absence of CSNAP impairs cell morphology, growth and cell cycle progression. (A) Confocal microscopy images of WT, ΔCSNAP and ΔCSNAP cells transfected with CSNAP-cerulean (Cer). Overexpression of CSNAP-cerulean in ΔCSNAP cells rescues the enlarged cell body phenotype (Scale bar: 20 μm). (B) ΔCSNAP cells have larger cell and nuclear area, which can be rescued by the exogenous expression of CSNAP-cerulean. Confocal images at 60× magnification of WT, ΔCSNAP and ΔCSNAP+CSNAP-cerulean expressing HAP1 cells were analyzed using Olympus Fluoview software. The area of at least 27 cells and nuclei were measured, and plotted as boxes extending from the third (Q3) to the first quartiles (Q1). Whiskers at the top and bottom represent measurements above the Q3 or below the Q1, respectively. (C) WT cells show higher colony forming potential than ΔCSNAP cells. WT and ΔCSNAP HAP1 cells were plated in triplicates, and incubated under culturing conditions for 8 days. Colonies were stained using Crystal violet, and counted using OpenCFU software. The graph represents results from 14 biological replicates, significance was calculated using Student's t-test (** $p<0.001$). (D) ΔCSNAP cells have altered cell cycle. Histograms of BrdU and propidium iodide stained asynchronous cells show that the lack of CSNAP results in a S-G2 shifted phenotype, that can be rescued by the expression of CSNAP-cerulean, but not when its C-terminal CSN interacting domain is absent. (E) Cells lacking CSNAP cell harbor larger population of dead cells. The bar chart shows the percentages of live and dead (pooled early apoptotic and dead cells) cell populations in the culture, measured by flow cytometry using annexin V-FITC and propidium iodide staining. Significance was calculated using Student's t-test (* $p<0.05$) using 6 replicates.

FIGS. 2A-E illustrate that DNA damage response is compromised in ΔCSNAP cells. (A) ΔCSNAP cells show higher proliferation rates after UV-induced DNA damage. The plot shows proliferation rates of WT and ΔCSNAP cells two hours after exposure to UV-C light, calculated as fold of initial proliferation for each cell line. UV-induced DNA damage caused a significant reduction of proliferation in WT cells (blue), while cells deficient in CSNAP (red) failed to down regulate to that extent. This UV-response phenotype is rescued by exogenous expression of the full length CSNAP protein (green), but not when its C-terminal CSN-interaction domain, is missing (orange). The graph represents the averages of three independent experiments with standard errors. Significance was calculated using 2 way Anova test, followed by a Tukey Post Hoc Test ($p<0.005$). (* $p<0.05$,  $p<0.01$, * $p<0.005$) (B) ΔCSNAP cells accumulate DNA damages following UV-C exposure. The genotoxic effect of UV-C was measured using alkaline comet assay. The Box-whisker plot of a representative experiment shows that ΔCSNAP cells have higher Olive tail moments after exposure to high dose UV. (C) Cells lacking CSNAP exhibit compromised recovery after exposure to high dose UV. WT and ΔCSNAP HAP1 cells were exposed to UV-C light and incubated under culturing conditions for 8 days. Colonies were stained using Crystal violet, and counted using OpenCFU software. ΔCSNAP cells have ~2.7-fold less colony forming potential following UV damage, compared to the WT cells. The graph represents results from 7 biological replicates, significance was calculated using Student's t-test ($p<0.05$). (D) UV-exposed ΔCSNAP cells stay longer in S and G2 phases. Comparison of relative distribution of cell populations in different phases of the cell cycle, as calculated from flow cytometry histograms of double thymidine synchronized cells with or without exposure to UV-C light. DNA damage caused by UV elongates S and G2 phases, and this effect is significantly more pronounced in cells lacking CSNAP. (E) In ΔCSNAP cells, the early apoptotic response is delayed following UV damage. The bar charts show averages of populations (6 independent experiments) as percentage of single cells, measured by flow cytometry using annexin V-FITC and propidium iodide staining. Live and early apoptotic cell populations are significantly different in ΔCSNAP cells after exposure to UV (* $p<0.0005$ and  $p<0.001$, respectively).

FIGS. 3A-D illustrate that the absence of CSNAP modulates the CSN interacting network. (A) CSN and its interacting proteins were pulled down using an antibody against CSN3 from cells expressing CSN with or without CSNAP. Immunoprecipitated proteins were then analyzed by label-free proteomics approach. Scatter plot comparing intensities of proteins in ΔCSNAP and WT samples show that a number of CRL proteins were found to be over- or underrepresented in the interactome of the $CSN^{\Delta CSNAP}$ and CSN complexes. In contrast, the levels of CSN subunits do not change significantly between WT and ΔCSNAP cells. (B) Reciprocal immunoprecipitation shows tighter interaction between CSN3 and FBXL15 (upper panel), and CSN3 and DDB2 (lower panel) in the absence of CSNAP. The levels of CSN subunits (C) and different Cullin isoforms (D) are comparable in WT and ΔCSNAP cells, thus the differences in the amount of the pulled down proteins are likely due to different affinities of interaction.

Figure 4:
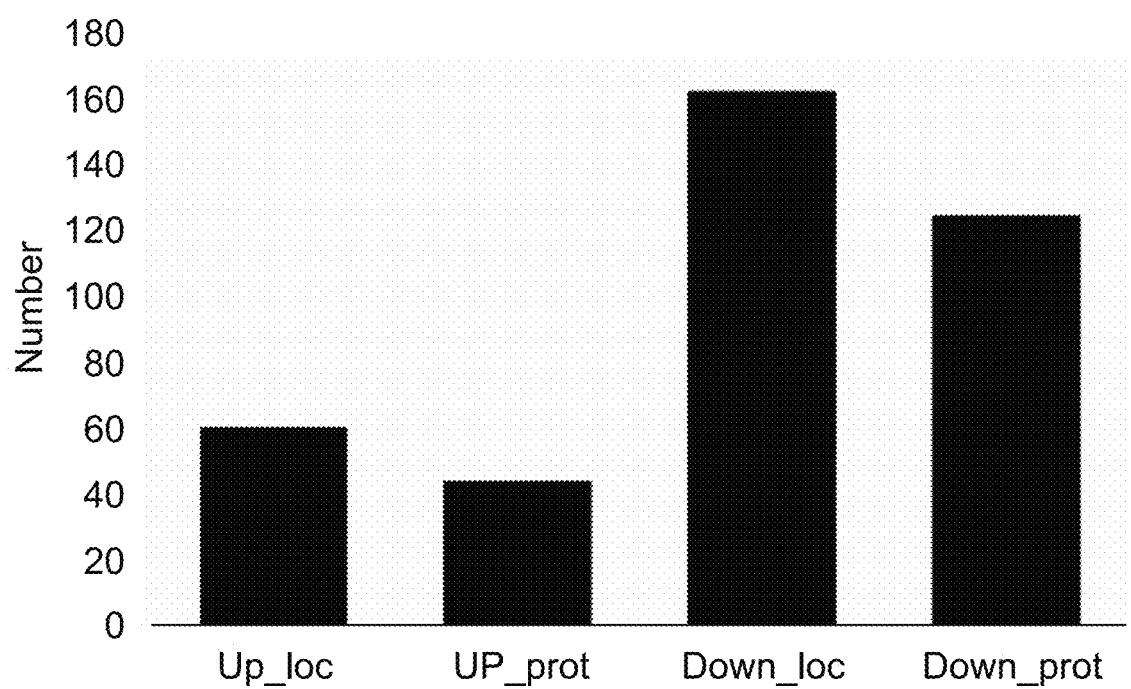

FIG. 4 is a bar graph illustrating the variations between WT and ΔCSNAP cells as measured by Ubiquitin affinity proteomics. SILAC-based quantitative K-ε-GG mass spectrometry startergy to identify variation in the abundance of ubiquitinated proteins. Bar plot showing the number of differentially ubiquitinated (ΔCSNAP/WT) sites (loc) and proteins (prot) that were increased (Up) or decreased (Down).

FIGS. 5A-D illustrate that the absence of CSNAP impacts the proteome. Label free total proteome analysis of WT and ΔCSNAP cells, with and without UV exposure. Proteomics data, after logarithmic transformation and flooring, was analyzed by two-way ANOVA using the 2 factors: strain and UV treatment. Proteins with p-value below 0.05 and an absolute fold change above 1.5 were considered as being differentially expressed. (A) Heatmap analysis of differentially expressed proteins grouped to 5 clusters. The expression value of each protein is plotted in blue-red color scale. Pathways that are enriched in a specific cluster are indicated on the right. Unlike WT cells, which display up- and down-regulation of various cellular functions, the proteome of ΔCSNAP cells is unaffected. (B) The bar plot shows the number of differentially expressed proteins in each of the four pair-wise comparisons, highlighting that in ΔCSNAP cells the DNA damage response is compromised. (C) Expression levels of 4 representative under- and overrepresented proteins, PARP1, NQO1, PDCD4, and vimentin, respectively, were validated using Western blots from WT and ΔCSNAP cell lysates. UV-treated samples were collected 2 hours following damage induction at 20 J/m$^2$. (D) PARP1 cleavage is delayed in cells lacking CSNAP. Chromatin-bound fractions were monitored by Western blot for caspase-mediated PARP1 cleavage, a marker for commitment to apoptosis.

Figure 6:
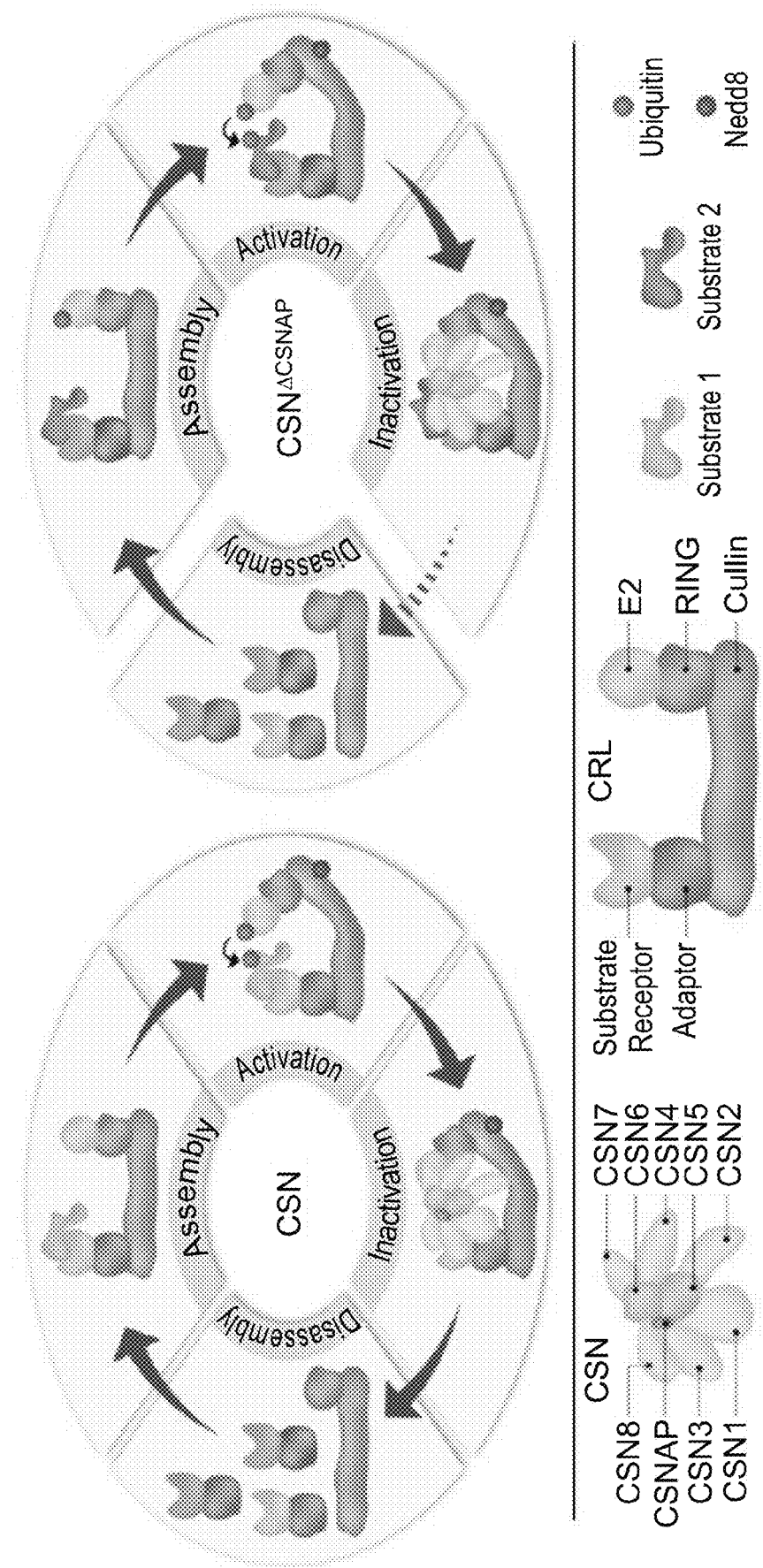

FIG. 6 is a cartoon illustrating how CSNAP modulates the CSN-CRL interactome. Diagram representation the CRL cycle (left panel). CRLs form dynamic complexes with different substrate receptors. The conjunction of Nedd8 to a conserved lysine residue in the cullin subunit, induces a conformational change that activates the CRL complex, promoting ubiquitin transfer to the substrate. The CSN complex inactivates CRL by two independent mechanisms, catalytic and non-catalytic. The first involves catalytic removal of the Nedd8 conjugate, while the second is mediated through physical binding to CRLs sterically precluding interactions with E2 enzymes and ubiquitination substrates. Subsequently, after CSN dissociation, CRLs can be dissembled and assembled into new configurations according to the cell needs, enabling other substrates to be ubiquitinated. The results indicate that CSNAP impacts the non-catalytic function of CSN (right panel). CSNAP reduces the affinity of CSN for CRL, and thus enables efficient disassembly and remodeling of CRL complexes. In the absence of CSNAP the disassembly and assembly steps of the cycle are compromised, affecting the reconfiguration of CRL assemblies and the ability to respond to cellular stimuli.

Figure 7:
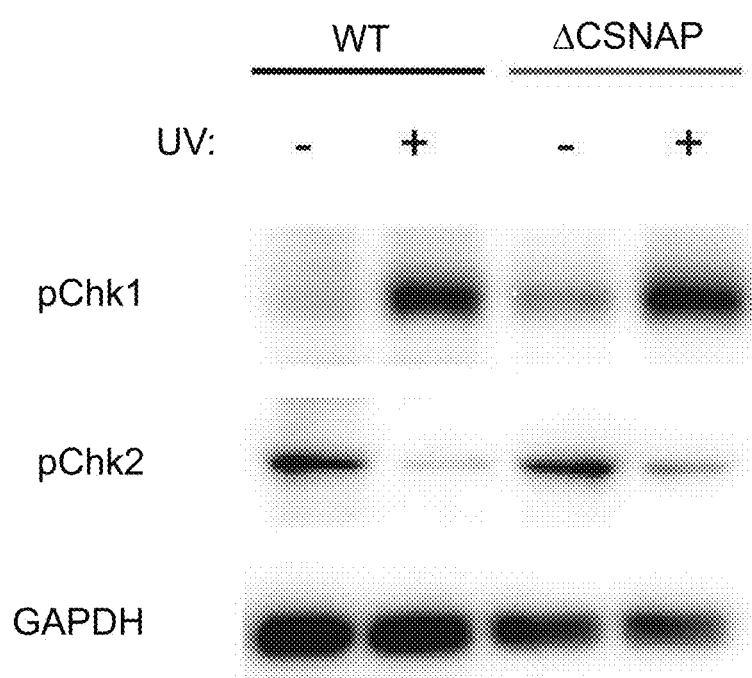

FIG. 7 illustrates that Checkpoint control is unaffected in cells lacking CSNAP. Untreated and UV-exposed (20 J/m$^2$) WT and ΔCSNAP cells were lysed 4 hours post-damage, and phosphorylation of Chk1 (Ser345) and Chk2 (Thr68) was compared using antibodies. In response to UV irradiation Chk1 is phosphorylated as expected, while Chk2, which is IR dependent, is not. Thus, the activation state of the Chk proteins is not dependent on the presence of CSNAP.

Figure 8:
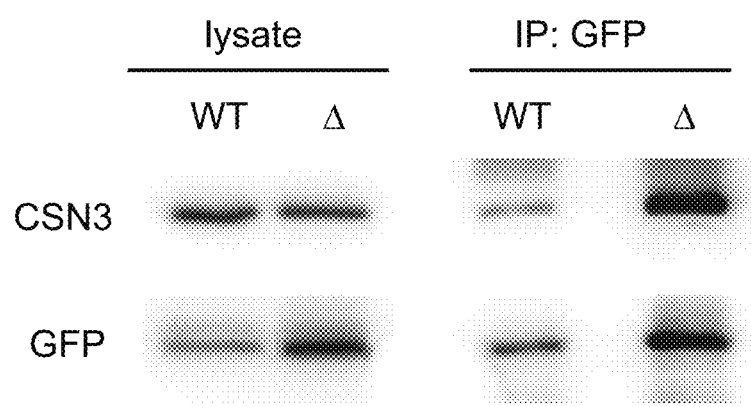

FIG. 8 illustrates that the C-terminal segment of CSNAP is incorporated into WT and ΔCSNAP CSN complexes. Lysates of WT and ΔCSNAP (D) cells stably expressing the C-terminus of CSNAP (C-CSNAP-Cerulean) were probed with antibodies for Csn3 and GFP (Cer). The CSN complex was then immunoprecipitated using an antibody against Cerulean (GFP) tag from both WT and ΔCSNAP (D) cells, indicating that C-CSNAP-Cerulean is incorporated into the WT CSN complex.

Figure 9:
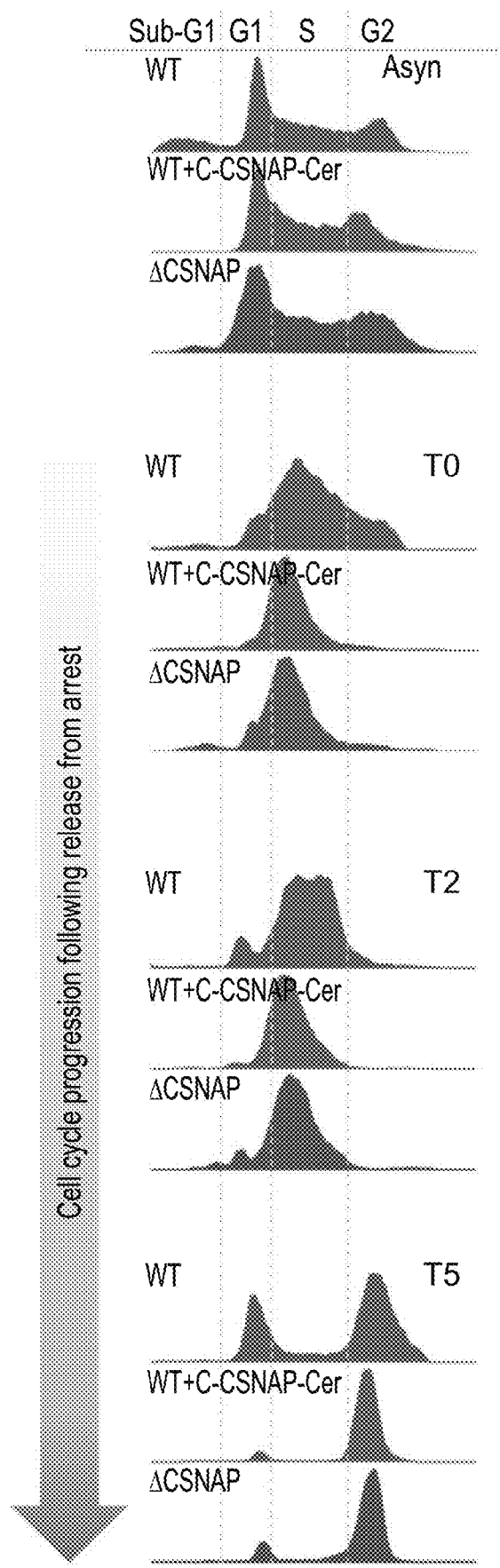

FIG. 9 illustrates that C-CSNAP expression slows cell cycle progression in WT cells. WT (blue), WT expressing C-CSNAP-Cerulean (purple) and ΔCSNAP (red) cells were arrested by double thymidine block at G1/S phase border. Flow cytometry analysis was performed after release from the blockage of cell cycle progression at (T0), after 2 (T2) and 5 hours (T5). Exogenous expression of C-CSNAP-Cerulean in WT cells slowed cell cycle progressed giving rise to a ΔCSNAP-like phenotype.

Figure 10:
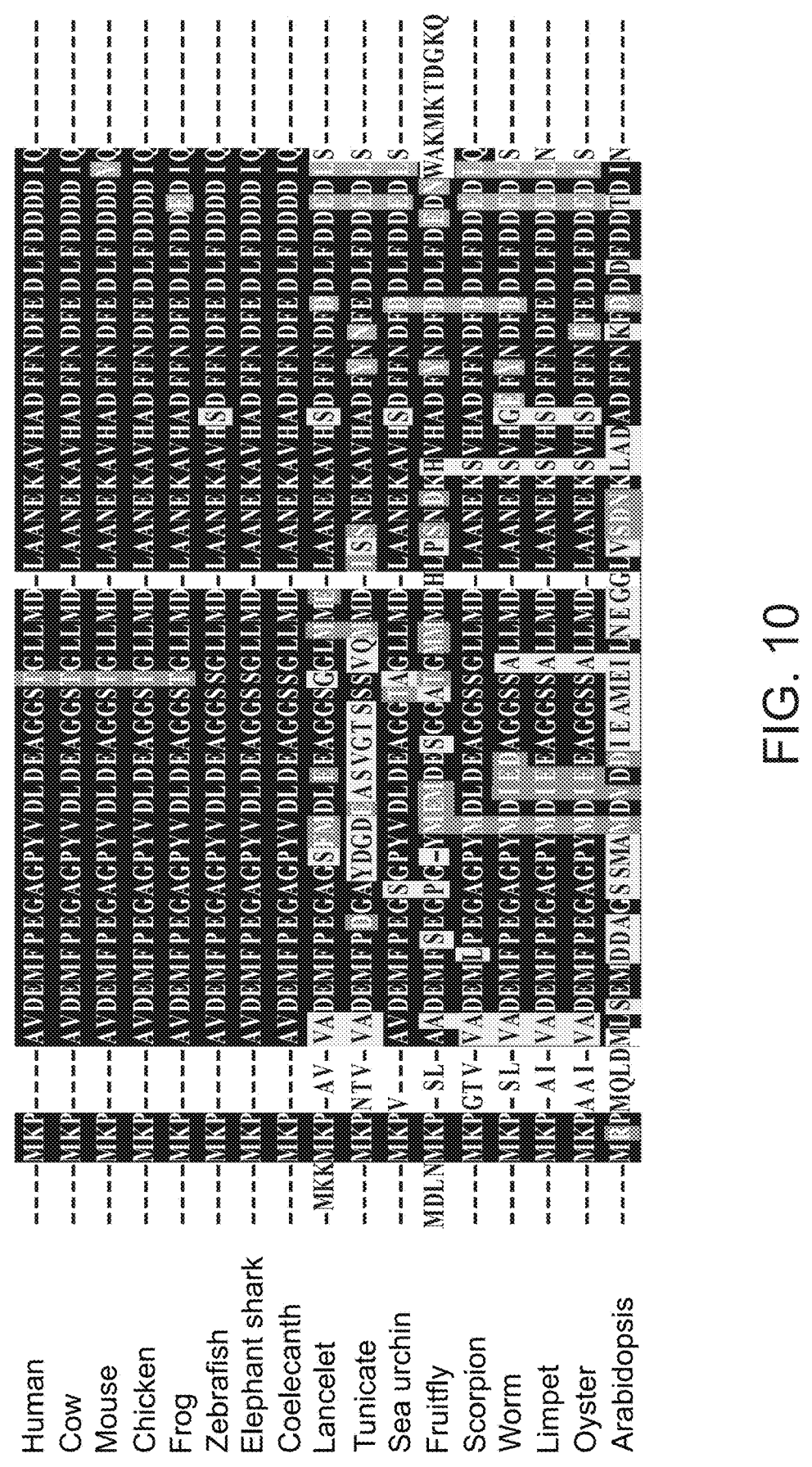

FIG. 10 illustrates that the protein sequence of CSNAP is highly conserved. Multiple sequence alignment of CSNAP sequences indicates that it is highly conserved all along its length, but particularly in the C-terminus, F/D-rich region. The alignment was performed with ClustalW version 2.1, and colored according to similarity. Residues conserved in all 17 sequences are highlighted in black, those conserved in part of the sequences are highlighted in grey.

Human sequence—SEQ ID NO: 19;
Cow sequence—SEQ ID NO: 20;
Mouse sequence—SEQ ID NO: 21;
Chicken sequence—SEQ ID NO: 22;
Frog sequence—SEQ ID NO: 23;
Zebrafish sequence—SEQ ID NO: 24;
Elephant shark sequence—SEQ ID NO: 25;
Coelecanth sequence—SEQ ID NO: 26;
Lancelet—SEQ ID NO: 27;
Tunicate—SEQ ID NO: 28;
Sea_urchin sequence—SEQ ID NO: 29;
Fruitfly sequence—SEQ ID NO: 30;
Scorpion sequence—SEQ ID NO: 31;
Worm sequence—SEQ ID NO: 32;
Limpet sequence—SEQ ID NO: 33;
Oyster sequence—SEQ ID NO: 34;
*Arabidopsis* sequence—SEQ ID NO: 35.

DESCRIPTION OF SPECIFIC EMBODIMENTS OF THE INVENTION

The present invention, in some embodiments thereof, relates to agents that regulate the COP9 signalosome (CSN) complex, more particularly, but not exclusively, to agents that reduce the incorporation of CSNAP into the CSN complex.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The cullin-RING ubiquitin E3 ligase (CRL) family consists of approximately 250 complexes that catalyze ubiquitylation of proteins to achieve cellular regulation. All CRLs are regulated by the COP9 signalosome complex (CSN) through both enzymatic and non-enzymatic mechanisms. The present inventors have now found that CSNAP, the ninth subunit of the CSN, has a pronounced impact on the non-enzymatic activity of the complex.

Cells lacking CSNAP display severe phenotypes including morphological growth defects (FIGS. 1A-B), impaired DNA damage response (FIGS. 2A-E, reproductive capacity and cell cycle progression (FIGS. 1C-D), all of which are tied to impaired CSN function. The data further demonstrate that CSNAP reduces the affinity of CSN towards CRLs and consequently it impacts CRL remodeling and adaptation to cellular needs.

Whilst reducing the present invention to practice, the present inventors synthesized a peptide comprising the C-terminal region of CSNAP, known to be responsible for assembly into the CSN complex. It was hypothesized that this peptide should prevent the incorporation of the endogenous CSNAP protein by blocking its binding site. The present inventors showed that cells exposed to the C-terminal peptide display a similar phenotype as ΔCSNAP (FIG. 9). Specifically, it was found that the peptide was capable of preventing cell cycle progression and induce cell death.

The CSN has been considered a target for cancer therapy for more than a decade. For example, major efforts have been directed over the years towards inhibition of the catalytic subunit, Csn5 (Jab1).

The present inventors therefore propose that agents that block CSNAP functioning (such as peptide agents that block CSNAP from incorporating into the CSN complex, e.g. by binding to the Csn3 binding site) may be used for the treatment of diseases associated with aberrant protein degradation, such as cancer.

Thus, according to a first aspect of the present invention, there is provided a method of treating a condition associated with aberrant protein degradation of a subject, comprising administering to the subject a therapeutically effective amount of an agent which reduces the amount of CSN Acidic Protein (CSNAP) which is incorporated into the COP9 signalosome complex (CSN) of the cell, thereby treating the condition associated with aberrant protein degradation.

As used herein, the term "CSNAP" refers to a subunit of the CSN complex having the Uniprot number Q8WXC6. The amino acid sequence of human CSNAP is set forth as follows MKPAVDEMFP EGAGPYVDLD EAGGSTGLLM DLAANEKAVH ADFFNDFEDL FDDDDIQ (SEQ ID NO: 2).

The phrase "COP9/signalosome (CSN)" refers to a protein complex with isopeptidase activity that catalyzes the hydrolysis of NEDD8 protein from the cullin subunit of Cullin-RING ubiquitin ligases (CRL). Therefore, it is responsible for CRL deneddylation. The CSN is also able to bind denedyllated cullin-RING complex and retain them in deactivated form. COP9 signalosome thus serves as a deactivator of CRLs.

In one embodiment, the agent blocks the binding of CSNAP to its endogenous binding site on the CSN. Thus, for example the agent may block CSNAP from binding to the Csn3 subunit or the Csn5/6 subunit of said CSNAP.

An example of such an agent is a peptide agent that comprises an amino acid sequence derived from a human or non-human CSNAP protein—for example the C-terminus of the CSNAP protein (or a peptidomimetic thereof). Thus, for example the peptide may comprise at least 5, 6, 7, 8, 9, 10, 11, 12, 13, 14, 15 or 16 contiguous amino acids of the amino acid sequence as set forth in SEQ ID NO: 1. Preferably, the peptide agent comprises at least the last five C-terminal amino acids of the sequence as set forth in SEQ ID NO: 1. Preferably, the peptide of this aspect of the present invention is devoid of at least the last 5, 10, 15, 20, 25, 26, 27, 28, 29, 30, 31, 32, 33, 34, 35, 36, 37, 38, 39, 40 or 41 amino acids from the N terminus of CSNAP.

Other peptide agents contemplated by the present invention are the C-terminal amino acids of non-human CSNAP—e.g. those presented in FIG. 10. Thus, for example the peptide may comprise at least 5, 6, 7, 8, 9, 10, 11, 12, 13, 14, 15 or 16 contiguous amino acids of the amino acid sequences presented in FIG. 10 which are aligned with the C terminus of the human CSNAP.

In one embodiment, the peptide of this aspect of the present invention comprises no more than 10 amino acids of the human CSNAP sequence, 11 amino acids of the human CSNAP sequence, 12 amino acids of the human CSNAP sequence, 13 amino acids of the human CSNAP sequence, 14 amino acids of the human CSNAP sequence, 15 amino acids of the human CSNAP sequence, 16 amino acids of the human CSNAP sequence, 17 amino acids of the human CSNAP sequence, 18 amino acids of the human CSNAP sequence, 19 amino acids of the human CSNAP sequence or 20 amino acids of the human CSNAP sequence.

In another embodiment, the peptide of this aspect of the present invention comprises no more than 10 amino acids of the non-human CSNAP sequence, 11 amino acids of the non-human CSNAP sequence, 12 amino acids of the non-human CSNAP sequence, 13 amino acids of the non-human CSNAP sequence, 14 amino acids of the non-human CSNAP sequence, 15 amino acids of the non-human CSNAP sequence, 16 amino acids of the non-human CSNAP sequence, 17 amino acids of the non-human CSNAP sequence, 18 amino acids of the non-human CSNAP sequence, 19 amino acids of the non-human CSNAP sequence or 20 amino acids of the non-human CSNAP sequence.

The term "peptide" as used herein refers to a polymer of natural or synthetic amino acids, encompassing native peptides (either degradation products, synthetically synthesized polypeptides or recombinant polypeptides) and peptidomimetics (typically, synthetically synthesized peptides), as well as peptoids and semipeptoids which are polypeptide analogs, which may have, for example, modifications rendering the peptides even more stable while in a body or more capable of penetrating into cells.

Such modifications include, but are not limited to N terminus modification, C terminus modification, polypeptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided herein under.

Polypeptide bonds (—CO—NH—) within the polypeptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), polypeptide derivatives (—N(R)—CH2-CO—), wherein R is the "normal" side chain, naturally presented on the carbon atom.

These modifications can occur at any of the bonds along the polypeptide chain and even at several (2-3) at the same time.

Natural aromatic amino acids, Trp, Tyr and Phe, may be substituted for synthetic non-natural acid such as Phenylglycine, TIC, naphthylelanine (Nol), ring-methylated derivatives of Phe, halogenated derivatives of Phe or o-methyl-Tyr.

In addition to the above, the polypeptides of the present invention may also include one or more modified amino acids or one or more non-amino acid monomers (e.g. fatty acids, complex carbohydrates etc.).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids (stereoisomers).

Tables 1 and 2 below list naturally occurring amino acids (Table 1) and non-conventional or modified amino acids (Table 2) which can be used with the present invention.

TABLE I

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| ornithine | Orn | hydroxyproline | Hyp |
| α-aminobutyric acid | Abu | aminonorbornyl-carboxylate | Norb |
| D-alanine | Dala | | |
| D-arginine | Darg | aminocyclopropane-carboxylate | Cpro |
| D-asparagine | Dasn | | |
| D-aspartic acid | Dasp | N-(3-guanidinopropyl)glycine | Narg |
| D-cysteine | Dcys | | |
| D-glutamine | Dgln | N-(carbamylmethyl)glycine | Nasn |
| D-glutamic acid | Dglu | N-(carboxymethyl)glycine | Nasp |
| D-histidine | Dhis | N-(thiomethyl)glycine | Ncys |
| D-isoleucine | Dile | N-(2-carbamylethyl)glycine | Ngln |
| D-leucine | Dleu | N-(2-carboxyethyl)glycine | Nglu |
| D-lysine | Dlys | N-(imidazolylethyl)glycine | Nhis |
| D-methionine | Dmet | N-(1-methylpropyl)glycine | Nile |
| D-ornithine | Dorn | N-(2-methylpropyl)glycine | Nleu |
| D-phenylalanine | Dphe | N-(4-aminobutyl)glycine | Nlys |
| D-proline | Dpro | N-(2-methylthioethyl)glycine | Nmet |
| D-serine | Dser | N-(3-aminopropyl)glycine | Norn |
| D-threonine | Dthr | N-benzylglycine | Nphe |
| D-tryptophan | Dtrp | N-(hydroxymethyl)glycine | Nser |
| D-tyrosine | Dtyr | N-(1-hydroxyethyl)glycine | Nthr |
| D-valine | Dval | N-(3-indolylethyl) glycine | Nhtrp |
| D-N-methylalanine | Dnmala | N-(p-hydroxyphenyl)glycine | Ntyr |
| D-N-methylarginine | Dnmarg | N-(1-methylethyl)glycine | Nval |
| D-N-methylasparagine | Dnmasn | N-methylglycine | Nmgly |
| D-N-methylasparatate | Dnmasp | L-N-methylalanine | Nmala |
| D-N-methylcysteine | Dnmcys | L-N-methylarginine | Nmarg |
| D-N-methylglutamine | Dnmgln | L-N-methylasparagine | Nmasn |
| D-N-methylglutamate | Dnmglu | L-N-methylaspartic acid | Nmasp |
| D-N-methylhistidine | Dnmhis | L-N-methylcysteine | Nmcys |
| D-N-methylisoleucine | Dnmile | L-N-methylglutamine | Nmgln |
| D-N-methylleucine | Dnmleu | L-N-methylglutamic acid | Nmglu |
| D-N-methyllysine | Dnmlys | L-N-methylhistidine | Nmhis |
| D-N-methylmethionine | Dnmmet | L-N-methylisolleucine | Nmile |
| D-N-methylornithine | Dnmorn | L-N-methylleucine | Nmleu |
| D-N-methylphenylalanine | Dnmphe | L-N-methyllysine | Nmlys |
| D-N-methylproline | Dnmpro | L-N-methylmethionine | Nmmet |
| D-N-methylserine | Dnmser | L-N-methylornithine | Nmorn |
| D-N-methylthreonine | Dnmthr | L-N-methylphenylalanine | Nmphe |
| D-N-methyltryptophan | Dnmtrp | L-N-methylproline | Nmpro |
| D-N-methyltyrosine | Dnmtyr | L-N-methylserine | Nmser |
| D-N-methylvaline | Dnmval | L-N-methylthreonine | Nmthr |
| L-norleucine | Nle | L-N-methyltryptophan | Nmtrp |
| L-norvaline | Nva | L-N-methyltyrosine | Nmtyr |
| L-ethylglycine | Etg | L-N-methylvaline | Nmval |
| L-t-butylglycine | Tbug | L-N-methylnorleucine | Nmnle |

TABLE 2-continued

| Non-conventional amino acid | Code | Non-conventional amino acid | Code |
|---|---|---|---|
| L-homophenylalanine | Hphe | L-N-methylnorvaline | Nmnva |
| α-naphthylalanine | Anap | L-N-methyl-ethylglycine | Nmetg |
| penicillamine | Pen | L-N-methyl-t-butylglycine | Nmtbug |
| γ-aminobutyric acid | Gabu | L-N-methyl-homophenylalanine | Nmhphe |
| cyclohexylalanine | Chexa | | |
| cyclopentylalanine | Cpen | N-methyl-α-naphthylalanine | Nmanap |
| α-amino-α-methylbutyrate | Aabu | N-methylpenicillamine | Nmpen |
| α-aminoisobutyric acid | Aib | N-methyl-γ-aminobutyrate | Nmgabu |
| D-α-methylarginine | Dmarg | N-methyl-cyclohexylalanine | Nmchexa |
| D-α-methylasparagine | Dmasn | N-methyl-cyclopentylalanine | Nmcpen |
| D-α-methylaspartate | Dmasp | N-methyl-α-amino-α-methylbutyrate | Nmaabu |
| D-α-methylcysteine | Dmcys | | |
| D-α-methylglutamine | Dmgln | N-methyl-α-aminoisobutyrate | Nmaib |
| D-α-methyl glutamic acid | Dmglu | | |
| D-α-methylhistidine | Dmhis | L-α-methylarginine | Marg |
| D-α-methylisoleucine | Dmile | L-α-methylasparagine | Masn |
| D-α-methylleucine | Dmleu | L-α-methylaspartate | Masp |
| D-α-methyllysine | Dmlys | L-α-methylcysteine | Mcys |
| D-α-methylmethionine | Dmmet | L-α-methylglutamine | Mgln |
| D-α-methylornithine | Dmorn | L-α-methylglutamate | Mglu |
| D-α-methylphenylalanine | Dmphe | L-α-methylhistidine | Mhis |
| D-α-methylproline | Dmpro | L-α-methylisoleucine | Mile |
| D-α-methylserine | Dmser | L-α-methylleucine | Mleu |
| D-α-methylthreonine | Dmthr | L-α-methyllysine | Mlys |
| D-α-methyltryptophan | Dmtrp | L-α-methylmethionine | Mmet |
| D-α-methyltyrosine | Dmtyr | L-α-methylornithine | Morn |
| D-α-methylvaline | Dmval | L-α-methylphenylalanine | Mphe |
| N-cyclobutylglycine | Ncbut | L-α-methylproline | Mpro |
| N-cycloheptylglycine | Nchep | L-α-methylserine | Mser |
| N-cyclohexylglycine | Nchex | L-α-methylthreonine | Mthr |
| N-cyclodecylglycine | Ncdec | L-α-methyltryptophan | Mtrp |
| N-cyclododecylglycine | Ncdod | L-α-methyltyrosine | Mtyr |
| N-cyclooctylglycine | Ncoct | L-α-methylvaline | Mval |
| N-cyclopropylglycine | Ncpro | L-α-methylnorvaline | Mnva |
| N-cycloundecylglycine | Ncund | L-α-methylethylglycine | Metg |
| N-(2-aminoethyl)glycine | Naeg | L-α-methyl-t-butylglycine | Mtbug |
| N-(2,2-diphenylethyl)glycine | Nbhm | L-α-methyl-homophenylalanine | Mhphe |
| N-(3,3-diphenylpropyl)glycine | Nbhe | α-methyl-α-naphthylalanine | Manap |
| | | α-methylpenicillamine | Mpen |
| 1-carboxy-1-(2,2-diphenyl ethylamino)cyclopropane | Nmbc | α-methyl-γ-aminobutyrate | Mgabu |
| | | α-methyl-cyclohexylalanine | Mchexa |
| phosphoserine | pSer | α-methyl-cyclopentylalanine | Mcpen |
| phosphotyrosine | pTyr | N-(N-(2,2-diphenylethyl) carbamylmethyl-glycine | Nnbhm |
| 2-aminoadipic acid | | | |
| | | N-(N-(3,3-diphenylpropyl) carbamylmethyl-glycine | Nnbhe |
| | | 1,2,3,4-tetrahydroisoquinoline-3-carboxylic acid | Tic |
| | | phosphothreonine | pThr |
| | | O-methyl-tyrosine | |
| | | hydroxylysine | |

The amino acids of the peptides of the present invention may be substituted either conservatively or non-conservatively.

The term "conservative substitution" as used herein, refers to the replacement of an amino acid present in the native sequence in the peptide with a naturally or non-naturally occurring amino or a peptidomimetics having similar steric properties. Where the side-chain of the native amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid).

As naturally occurring amino acids are typically grouped according to their properties, conservative substitutions by naturally occurring amino acids can be easily determined bearing in mind the fact that in accordance with the invention replacement of charged amino acids by sterically similar non-charged amino acids are considered as conservative substitutions.

For producing conservative substitutions by non-naturally occurring amino acids it is also possible to use amino acid analogs (synthetic amino acids) well known in the art. A peptidomimetic of the naturally occurring amino acid is well documented in the literature known to the skilled practitioner.

When affecting conservative substitutions the substituting amino acid should have the same or a similar functional group in the side chain as the original amino acid.

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted. Examples of non-conservative substitutions of this type include the substitution of phenylalanine or cyclohexylmethyl glycine for alanine, isoleucine for glycine, or —NH—CHR—CH$_2$)$_5$—COOHFCO— for aspartic acid. Those non-conservative substitutions which fall under the scope of the present invention are those, which still constitute a peptide having anti-bacterial properties.

As mentioned, the N and C termini of the peptides of the present invention may be protected by function groups. Suitable functional groups are described in Green and Wuts, "Protecting Groups in Organic Synthesis", John Wiley and Sons, Chapters 5 and 7, 1991, the teachings of which are incorporated herein by reference. Preferred protecting groups are those that facilitate transport of the compound attached thereto into a cell, for example, by reducing the hydrophilicity and increasing the lipophilicity of the compounds.

These moieties can be cleaved in vivo, either by hydrolysis or enzymatically, inside the cell. Hydroxyl protecting groups include esters, carbonates and carbamate protecting groups. Amine protecting groups include alkoxy and aryloxy carbonyl groups, as described above for N-terminal protecting groups. Carboxylic acid protecting groups include aliphatic, benzylic and aryl esters, as described above for C-terminal protecting groups. In one embodiment, the carboxylic acid group in the side chain of one or more glutamic acid or aspartic acid residue in a peptide of the present invention is protected, preferably with a methyl, ethyl, benzyl or substituted benzyl ester.

Examples of N-terminal protecting groups include acyl groups (—CO—R1) and alkoxy carbonyl or aryloxy carbonyl groups (—CO—O—R1), wherein R1 is an aliphatic, substituted aliphatic, benzyl, substituted benzyl, aromatic or a substituted aromatic group. Specific examples of acyl groups include acetyl, (ethyl)-CO—, n-propyl-CO—, iso-propyl-CO—, n-butyl-CO—, sec-butyl-CO—, t-butyl-CO—, hexyl, lauroyl, palmitoyl, myristoyl, stearyl, oleoyl phenyl-CO—, substituted phenyl-CO—, benzyl-CO— and (substituted benzyl)-CO—. Examples of alkoxy carbonyl and aryloxy carbonyl groups include CH3-O—CO—, (ethyl)-O—CO—, n-propyl-O—CO—, iso-propyl-O—CO—, n-butyl-O—CO—, sec-butyl-O—CO—, t-butyl-O—CO—, phenyl-O—CO—, substituted phenyl-O—CO— and benzyl-O—CO—, (substituted benzyl)-O—CO—. Adamantan, naphtalen, myristoleyl, tuluen, biphenyl, cinnamoyl, nitrobenzoy, toluoyl, furoyl, benzoyl, cyclohexane, norbornane, Z-caproic. In order to facilitate the N-acylation, one to four glycine residues can be present in the N-terminus of the molecule.

The carboxyl group at the C-terminus of the compound can be protected, for example, by an amide (i.e., the hydroxyl group at the C-terminus is replaced with —NH$_2$, —NHR$_2$ and —NR$_2$R$_3$) or ester (i.e. the hydroxyl group at the C-terminus is replaced with —OR$_2$). R$_2$ and R$_3$ are independently an aliphatic, substituted aliphatic, benzyl, substituted benzyl, aryl or a substituted aryl group. In addition, taken together with the nitrogen atom, R$_2$ and R$_3$ can form a C4 to C8 heterocyclic ring with from about 0-2 additional heteroatoms such as nitrogen, oxygen or sulfur. Examples of suitable heterocyclic rings include piperidinyl, pyrrolidinyl, morpholino, thiomorpholino or piperazinyl. Examples of C-terminal protecting groups include —NH$_2$, —NHCH$_3$, —N(CH$_3$)$_2$, —NH(ethyl), —N(ethyl) 2, —N(methyl) (ethyl), —NH(benzyl), —N(C1-C4 alkyl) (benzyl), —NH(phenyl), —N(C1-C4 alkyl) (phenyl), —OCH$_3$, —O-(ethyl), —O-(n-propyl), —O-(n-butyl), —O-(iso-propyl), —O-(sec-butyl), —O-(t-butyl), —O-benzyl and —O-phenyl.

The peptides of the present invention may also comprise non-amino acid moieties, such as for example, hydrophobic moieties (various linear, branched, cyclic, polycyclic or hetrocyclic hydrocarbons and hydrocarbon derivatives) attached to the peptides; non-peptide penetrating agents; various protecting groups, especially where the compound is linear, which are attached to the compound's terminals to decrease degradation. Chemical (non-amino acid) groups present in the compound may be included in order to improve various physiological properties such; decreased degradation or clearance; decreased repulsion by various cellular pumps, improve immunogenic activities, improve various modes of administration (such as attachment of various sequences which allow penetration through various barriers, through the gut, etc.); increased specificity, increased affinity, decreased toxicity and the like.

Attaching the amino acid sequence component of the peptides of the invention to other non-amino acid agents may be by covalent linking, by non-covalent complexion, for example, by complexion to a hydrophobic polymer, which can be degraded or cleaved producing a compound capable of sustained release; by entrapping the amino acid part of the peptide in liposomes or micelles to produce the final peptide of the invention. The association may be by the entrapment of the amino acid sequence within the other component (liposome, micelle) or the impregnation of the amino acid sequence within a polymer to produce the final peptide of the invention.

The peptides of the invention may be linear or cyclic (cyclization may improve stability). Cyclization may take place by any means known in the art. Where the compound is composed predominantly of amino acids, cyclization may be via N- to C-terminal, N-terminal to side chain and N-terminal to backbone, C-terminal to side chain, C-terminal to backbone, side chain to backbone and side chain to side chain, as well as backbone to backbone cyclization. Cyclization of the peptide may also take place through non-amino acid organic moieties comprised in the peptide.

The peptides of the present invention can be biochemically synthesized such as by using standard solid phase techniques. These methods include exclusive solid phase synthesis, partial solid phase synthesis methods, fragment condensation, classical solution synthesis. Solid phase polypeptide synthesis procedures are well known in the art and further described by John Morrow Stewart and Janis Dillaha Young, Solid Phase Polypeptide Syntheses (2nd Ed., Pierce Chemical Company, 1984).

Large scale peptide synthesis is described by Andersson Biopolymers 2000; 55(3):227-50.

Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

Recombinant techniques may also be used to generate the peptides of the present invention. To produce a peptide of the present invention using recombinant technology, a polynucleotide encoding the peptide of the present invention is ligated into a nucleic acid expression vector, which comprises the polynucleotide sequence under the transcriptional control of a cis-regulatory sequence (e.g., promoter sequence) suitable for directing constitutive, tissue specific or inducible transcription of the polypeptides of the present invention in the host cells.

In addition to being synthesizable in host cells, the peptides of the present invention can also be synthesized using in vitro expression systems. These methods are well known in the art and the components of the system are commercially available.

It will be appreciated that the peptides described herein may be attached to a cell penetrating agent.

As used herein the phrase "penetrating agent" refers to an agent which enhances translocation of any of the attached peptide across a cell membrane.

According to one embodiment, the penetrating agent is a peptide and is attached to the CSNAP related peptide (either directly or non-directly) via a peptide bond.

Typically, peptide penetrating agents have an amino acid composition containing either a high relative abundance of positively charged amino acids such as lysine or arginine, or have sequences that contain an alternating pattern of polar/charged amino acids and non-polar, hydrophobic amino acids.

Examples of peptide penetrating agents include long and short versions of TAT (YGRKKRR—SEQ ID NO: 3 and YGRKKRRQRRR—SEQ ID NO: 4) and PTD (RRQRR—SEQ ID NO: 5. By way of non-limiting example, cell penetrating peptide (CPP) sequences may be used in order to enhance intracellular penetration. CPPs may include:

GRKKRRQRRRPPQ - ;  SEQ ID NO: 7

GRKKRRQRRRPP - ;  SEQ ID NO: 8

GRKKRRQRRRP- ;  SEQ ID NO: 9

GRKKRRQRRR- ;  SEQ ID NO: 10

GRKKRRQRR - ;  SEQ ID NO: 11

GRKKRRQR - ;  SEQ ID NO: 12

GRKKRRQ- ;  SEQ ID NO: 13

YGRKKRR - ;  SEQ ID NO: 14

YGRKKRRQRRR—SEQ ID NO: 15;
RRQRR—SEQ ID NO: 16.

According to a particular embodiment, the CSNAP peptides are attached to the cell penetrating peptides via a linking moiety.

Examples of linking moieties include but are not limited to a simple covalent bond, a flexible peptide linker, a disulfide bridge or a polymer such as polyethylene glycol (PEG). Peptide linkers may be entirely artificial (e.g., comprising 2 to 20 amino acid residues independently selected from the group consisting of glycine, serine, asparagine, threonine and alanine) or adopted from naturally occurring proteins. Disulfide bridge formation can be achieved, e.g., by addition of cysteine residues, as further described herein below.

Selection of the link between the two peptides should take into account that the link should not substantially interfere with the ability of the CSNAP peptide to block CSNAP from binding to the CSN or the ability of the cell penetrating peptide to traverse the cell membrane.

Thus, for example, the linking moiety is optionally a moiety, which is covalently attached to a side chain, an N-terminus or a C-terminus of the CSNAP peptide, as well as to a side chain, an N-terminus or a C-terminus of the cell penetrating peptide.

The linking moiety may be attached to the C-terminus of the CSNAP peptide and to the N-terminus of the cell penetrating peptide.

Alternatively, the linking moiety may be attached to the N-terminus of the CSNAP peptide and to the C-terminus of the cell penetrating peptide.

The linker may comprise additional amino acids linked together by peptide bonds which serve as spacers such that the linker does not interfere with the biological activity of the final compound. The linker is preferably made up of amino acids linked together by peptide bonds. Thus, in preferred embodiments, the linker is made up of from 1 to 10 amino acids linked by peptide bonds, wherein the amino acids are selected from the 20 naturally occurring amino acids. Some of these amino acids may be glycosylated, as is well understood by those in the art.

In a more preferred embodiment, besides serine and glutamic acid the amino acids in the linker are selected from glycine, alanine, proline, asparagine and lysine. Even more preferably, besides serine and glutamic acid, the linker is made up of a majority of amino acids that are sterically unhindered, such as glycine and alanine.

According to another embodiment, the linking peptide comprises a disulfide bridge.

Thus, in some embodiments of the invention, each of the peptides comprises an amino acid sequence as described herein above and further comprise at least one cysteine residue, such that the peptides are covalently linked to one another via a disulfide bridge formed between a cysteine residue in one peptide and a cysteine residue in another peptide.

Herein throughout, the phrases "disulfide bridge" and "disulfide bond" are used interchangeably, and describe a —S—S— bond.

The full length peptide (i.e. CSNAP peptide, optional linking peptide and optional cell penetrating peptide) is typically no longer than 20 amino acids, 21 amino acids, 22 amino acids, 23 amino acids, 24 amino acids, 25 amino acids, 26 amino acids, 27 amino acids, 28 amino acids, 29 amino acids or 30 amino acids.

It will be appreciated that as well as being useful for therapy, the peptide agents described herein are also contemplated to be of benefit for scientific and research purposes. The CSN has two mechanisms of function: the first by physical binding (steric mechanism) and second by covalent deneddylation (catalytic mechanism). By using the CSNAP derived peptides of the present invention, it is possible to uncouple the two activities, affecting only the steric mechanism.

As well as peptide agents, the present inventors contemplate additional agents capable of reducing the overall amount of CSNAP in the cell—which in turn reduces the amount of binding of CSNAP to COPS.

Such additional agents include polynucleotide agents, which are directed against a polynucleotide encoding CSNAP.

Polynucleotide agents may be administered as part of an expression construct. In this case, the polynucleotide agent is ligated in a nucleic acid construct under the control of a cis-acting regulatory element (e.g. promoter) capable of directing an expression of the agent in a constitutive or inducible manner.

The nucleic acid agent may be delivered using an appropriate gene delivery vehicle/method (transfection, transduction, etc.). Optionally an appropriate expression system is used. Examples of suitable constructs include, but are not limited to, pcDNA3, pcDNA3.1 (+/−), pGL3, PzeoSV2 (+/−), pDisplay, pEF/myc/cyto, pCMV/myc/cyto each of which is commercially available from Invitrogen Co. (www (dot)invitrogen(dot)com).

The expression construct may also be a virus. Examples of viral constructs include but are not limited to adenoviral vectors, retroviral vectors, vaccinia viral vectors, adeno-associated viral vectors, polyoma viral vectors, alphaviral vectors, rhabdoviral vectors, lenti viral vectors and herpes-viral vectors.

A viral construct such as a retroviral construct includes at least one transcriptional promoter/enhancer or locus-defining element(s), or other elements that control gene expression by other means such as alternate splicing, nuclear RNA export, or post-transcriptional modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably, the signal sequence for this purpose is a mammalian signal sequence or the signal sequence of the peptide variants of the present invention. Optionally, the construct may also include a signal that directs polyadenylation, as well as one or more restriction site and a translation termination sequence. By way of example, such constructs will typically include a 5' LTR, a tRNA binding site, a packaging signal, an origin of second-strand DNA synthesis, and a 3' LTR or a portion thereof.

Preferably the viral dose for infection is at least $10^3$, $10^4$, $10^5$, $10^6$, $10^7$, $10^8$, $10^9$, $10^{10}$, $10^{11}$, $10^{12}$, $10^{13}$, $10^{14}$, $10^{15}$ or higher pfu or viral particles.

Double stranded RNA may be synthesized by adding two opposing promoters to the ends of the gene segments, wherein one promoter is placed immediately 5' to the gene and the opposing promoter is placed immediately 3' to the gene segment. The dsRNA may then be transcribed with the appropriate polymerase.

In one embodiment, the polynucleotide is an RNA silencing agent.

As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA, which is capable of inhibiting or "silencing" the expression of a target gene. In certain embodiments, the RNA silencing agent is capable of preventing complete processing (e.g, the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

RNA interference refers to the process of sequence-specific post-transcriptional gene silencing in animals mediated by short interfering RNAs (siRNAs). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Accordingly, the present invention contemplates use of dsRNA to downregulate protein expression from mRNA.

According to one embodiment, the dsRNA is greater than 30 bp. The use of long dsRNAs (i.e. dsRNA greater than 30 bp) has been very limited owing to the belief that these longer regions of double stranded RNA will result in the induction of the interferon and PKR response. However, the use of long dsRNAs can provide numerous advantages in that the cell can select the optimal silencing sequence alleviating the need to test numerous siRNAs; long dsRNAs will allow for silencing libraries to have less complexity than would be necessary for siRNAs; and, perhaps most importantly, long dsRNA could prevent viral escape mutations when used as therapeutics.

Various studies demonstrate that long dsRNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl Acad. Sci. USA. 2002; 99:1443-1448; Tran N., et al., FEBS Lett. 2004; 573:127-134].

In particular, the present invention also contemplates introduction of long dsRNA (over 30 base transcripts) for gene silencing in cells where the interferon pathway is not activated (e.g. embryonic cells and oocytes) see for example Billy et al., PNAS 2001, Vol 98, pages 14428-14433 and Diallo et al, Oligonucleotides, Oct. 1, 2003, 13(5): 381-392. doi: 10.1089/154545703322617069.

The present invention also contemplates introduction of long dsRNA specifically designed not to induce the interferon and PKR pathways for down-regulating gene expression. For example, Shinagwa and Ishii [*Genes & Dev.* 17 (11): 1340-1345, 2003] have developed a vector, named pDECAP, to express long double-strand RNA from an RNA polymerase II (Pol II) promoter. Because the transcripts from pDECAP lack both the 5'-cap structure and the 3'-poly (A) tail that facilitate ds-RNA export to the cytoplasm, long ds-RNA from pDECAP does not induce the interferon response.

Another method of evading the interferon and PKR pathways in mammalian systems is by introduction of small inhibitory RNAs (siRNAs) either via transfection or endogenous expression.

The term "siRNA" refers to small inhibitory RNA duplexes (generally between 18-30 basepairs) that induce the RNA interference (RNAi) pathway. Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is theorized to result from providing Dicer with a substrate (27mer) instead of a product (21mer) and that this improves the rate or efficiency of entry of the siRNA duplex into RISC.

It has been found that position of the 3'-overhang influences potency of a siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

It will be appreciated that more than one siRNA agent may be used to down-regulate a target gene. Thus, for example, the present invention contemplates use of at least two siRNAs that target CSNAP.

The strands of a double-stranded interfering RNA (e.g., a siRNA) may be connected to form a hairpin or stem-loop structure (e.g., a shRNA). Thus, as mentioned the RNA silencing agent of the present invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3' (SEQ ID NO: 17; Brummelkamp, T. R. et al. (2002) Science 296: 550) and 5'-UUUGUGUAG-3' (SEQ ID NO: 18; Castanotto, D. et al. (2002) RNA 8:1454). It will be recognized by one of skill in the art that the resulting single chain oligonucleotide forms a stem-loop or hairpin structure comprising a double-stranded region capable of interacting with the RNAi machinery.

According to another embodiment the RNA silencing agent may be a miRNA. miRNAs are small RNAs made from genes encoding primary transcripts of various sizes. They have been identified in both animals and plants. The primary transcript (termed the "pri-miRNA") is processed through various nucleolytic steps to a shorter precursor miRNA, or "pre-miRNA." The pre-miRNA is present in a folded form so that the final (mature) miRNA is present in a duplex, the two strands being referred to as the miRNA (the strand that will eventually basepair with the target) The pre-miRNA is a substrate for a form of dicer that removes the miRNA duplex from the precursor, after which, similarly to siRNAs, the duplex can be taken into the RISC complex. It has been demonstrated that miRNAs can be transgenically expressed and be effective through expression of a precursor form, rather than the entire primary form (Parizotto et al. (2004) Genes & Development 18:2237-2242 and Guo et al. (2005) Plant Cell 17:1376-1386).

Unlike, siRNAs, miRNAs bind to transcript sequences with only partial complementarity (Zeng et al., 2002, Molec. Cell 9:1327-1333) and repress translation without affecting steady-state RNA levels (Lee et al., 1993, Cell 75:843-854; Wightman et al., 1993, Cell 75:855-862). Both miRNAs and siRNAs are processed by Dicer and associate with components of the RNA-induced silencing complex (Hutvagner et al., 2001, Science 293:834-838; Grishok et al., 2001, Cell 106: 23-34; Ketting et al., 2001, Genes Dev. 15:2654-2659; Williams et al., 2002, Proc. Natl. Acad. Sci. USA 99:6889-6894; Hammond et al., 2001, Science 293:1146-1150; Mourlatos et al., 2002, Genes Dev. 16:720-728). A recent report (Hutvagner et al., 2002, Sciencexpress 297:2056-2060) hypothesizes that gene regulation through the miRNA pathway versus the siRNA pathway is determined solely by the degree of complementarity to the target transcript. It is speculated that siRNAs with only partial identity to the mRNA target will function in translational repression, similar to a miRNA, rather than triggering RNA degradation.

It will be appreciated that the RNA silencing agent of the present invention need not be limited to those molecules containing only RNA, but further encompasses chemically-modified nucleotides and non-nucleotides.

Additional agents capable of downregulating CSNAP include ribozymes, DNAzymes and agents of the CRISPR system (e.g. CRISPR/Cas).

Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., Clin Diagn Virol. 10:163-71 (1998)]. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated— WEB home page).

Another agent capable of downregulating CSNAP is a RNA-guided endonuclease technology e.g. CRISPR system.

As used herein, the term "CRISPR system" also known as Clustered Regularly Interspaced Short Palindromic Repeats refers collectively to transcripts and other elements involved in the expression of or directing the activity of CRISPR-associated genes, including sequences encoding a Cas gene (e.g. CRISPR-associated endonuclease 9), a tracr (trans-activating CRISPR) sequence (e.g. tracrRNA or an active partial tracrRNA), a tracr-mate sequence (encompassing a "direct repeat" and a tracrRNA-processed partial direct repeat) or a guide sequence (also referred to as a "spacer") including but not limited to a crRNA sequence (i.e. an endogenous bacterial RNA that confers target specificity yet requires tracrRNA to bind to Cas) or a sgRNA sequence (i.e. single guide RNA).

In some embodiments, one or more elements of a CRISPR system is derived from a type I, type II, or type III CRISPR system. In some embodiments, one or more elements of a CRISPR system (e.g. Cas) is derived from a particular organism comprising an endogenous CRISPR system, such as *Streptococcus pyogenes, Neisseria meningitides, Streptococcus thermophilus* or *Treponema denticola*.

In general, a CRISPR system is characterized by elements that promote the formation of a CRISPR complex at the site of a target sequence (also referred to as a protospacer in the context of an endogenous CRISPR system).

In the context of formation of a CRISPR complex, "target sequence" refers to a sequence to which a guide sequence (i.e. guide RNA e.g. sgRNA or crRNA) is designed to have complementarity, where hybridization between a target sequence and a guide sequence promotes the formation of a CRISPR complex. Full complementarity is not necessarily required, provided there is sufficient complementarity to cause hybridization and promote formation of a CRISPR complex. Thus, according to some embodiments, global homology to the target sequence may be of 50%, 60%, 70%, 75%, 80%, 85%, 90%, 95% or 99%. A target sequence may comprise any polynucleotide, such as DNA or RNA polynucleotides. In some embodiments, a target sequence is located in the nucleus or cytoplasm of a cell.

Thus, the CRISPR system comprises two distinct components, a guide RNA (gRNA) that hybridizes with the target sequence (i.e. CSNAP encoding sequence), and a nuclease (e.g. Type-II Cas9 protein), wherein the gRNA targets the target sequence and the nuclease (e.g. Cas9 protein) cleaves the target sequence. The guide RNA may comprise a combination of an endogenous bacterial crRNA and tracrRNA, i.e. the gRNA combines the targeting specificity of the crRNA with the scaffolding properties of the tracrRNA (required for Cas9 binding). Alternatively, the guide RNA may be a single guide RNA capable of directly binding Cas.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence.

In some embodiments, the tracr sequence has sufficient complementarity to a tracr mate sequence to hybridize and participate in formation of a CRISPR complex. As with the target sequence, a complete complementarity is not needed, provided there is sufficient to be functional. In some embodiments, the tracr sequence has at least 50%, 60%, 70%, 80%, 90%, 95% or 99% of sequence complementarity along the length of the tracr mate sequence when optimally aligned.

Introducing CRISPR/Cas into a cell may be effected using one or more vectors driving expression of one or more elements of a CRISPR system such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. A single promoter may drive expression of a transcript encoding a CRISPR enzyme and one or more of the guide sequence, tracr mate sequence (optionally operably linked to the guide sequence), and a tracr sequence embedded within one or more intron sequences (e.g. each in a different intron, two or more in at least one intron, or all in a single intron).

An additional method of regulating the expression of an CSNAP gene in cells is via triplex forming oligonucleotides (TFOs). Recent studies have shown that TFOs can be designed which can recognize and bind to polypurine/polypyrimidine regions in double-stranded helical DNA in a sequence-specific manner. These recognition rules are outlined by Maher III, L. J., et al., Science, 1989; 245:725-730; Moser, H. E., et al., Science, 1987; 238:645-630; Beal, P. A., et al, Science, 1992; 251:1360-1363; Cooney, M., et al., Science, 1988; 241:456-459; and Hogan, M. E., et al., EP Publication 375408. Modification of the oligonucleotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer, J Clin Invest 2003; 112:487-94).

In general, the triplex-forming oligonucleotide has the sequence correspondence:

| oligo | 3'--A | G | G | T |
|---|---|---|---|---|
| duplex | 5'--A | G | C | T |
| duplex | 3'--T | C | G | A |

However, it has been shown that the A-AT and G-GC triplets have the greatest triple helical stability (Reither and Jeltsch, BMC Biochem, 2002, Sep. 12, Epub). The same authors have demonstrated that TFOs designed according to the A-AT and G-GC rule do not form non-specific triplexes, indicating that the triplex formation is indeed sequence specific.

Thus for any given sequence in the CSNAP a triplex forming sequence may be devised. Triplex-forming oligonucleotides preferably are at least 15, more preferably 25, still more preferably 30 or more nucleotides in length, up to 50 or 100 bp.

Transfection of cells (for example, via cationic liposomes) with TFOs, and formation of the triple helical structure with the target DNA induces steric and functional changes, blocking transcription initiation and elongation, allowing the introduction of desired sequence changes in the endogenous DNA and resulting in the specific downregulation of gene expression. Examples of such suppression of gene expression in cells treated with TFOs include knockout of episomal supFG1 and endogenous HPRT genes in mammalian cells (Vasquez et al., Nucl Acids Res. 1999; 27:1176-81, and Puri, et al, J Biol Chem, 2001; 276:28991-98), and the sequence- and target specific downregulation of expression of the Ets2 transcription factor, important in prostate cancer etiology (Carbone, et al, Nucl Acid Res. 2003; 31:833-43), and the pro-inflammatory ICAM-1 gene (Besch et al, J Biol Chem, 2002; 277:32473-79). In addition, Vuyisich and Beal have recently shown that sequence specific TFOs can bind to dsRNA, inhibiting activity of dsRNA-dependent enzymes such as RNA-dependent kinases (Vuyisich and Beal, Nuc. Acids Res 2000; 28:2369-74).

Additionally, TFOs designed according to the abovementioned principles can induce directed mutagenesis capable of effecting DNA repair, thus providing both downregulation and upregulation of expression of endogenous genes (Seidman and Glazer, J Clin Invest 2003; 112:487-94). Detailed description of the design, synthesis and administration of effective TFOs can be found in U.S. Patent Application Nos. 2003 017068 and 2003 0096980 to Froehler et al, and 2002 0128218 and 2002 0123476 to Emanuele et al, and U.S. Pat. No. 5,721,138 to Lawn.

Because unregulated, proteasome-mediated degradation of vital cell cycle regulatory proteins is an essential component of tumor development, a possible way of arresting or limiting tumor development is by regulation of the proteasome. This may be carried out directly or indirectly, for example by regulating the CSN of the cell. Transformed cells seem to be particularly sensitive to any disturbances of the cell cycle. Consequently, CSN regulators are being actively explored for the treatment of a variety of hematologic malignant neoplasms and solid tumors.

Thus, according to one embodiment, the disease or condition associated with aberrant protein degradation is cancer.

Examples of cancers that may be treated using the CSN regulators of this aspect of the present invention include, but are not limited to adrenocortical carcinoma, hereditary; bladder cancer; breast cancer; breast cancer, ductal; breast cancer, invasive intraductal; breast cancer, sporadic; breast cancer, susceptibility to; breast cancer, type 4; breast cancer, type 4; breast cancer-1; breast cancer-3; breast-ovarian cancer; triple negative breast cancer, Burkitt's lymphoma; cervical carcinoma; colorectal adenoma; colorectal cancer; colorectal cancer, hereditary nonpolyposis, type 1; colorectal cancer, hereditary nonpolyposis, type 2; colorectal cancer, hereditary nonpolyposis, type 3; colorectal cancer, hereditary nonpolyposis, type 6; colorectal cancer, hereditary nonpolyposis, type 7; dermatofibrosarcoma protuberans; endometrial carcinoma; esophageal cancer; gastric cancer, fibrosarcoma, glioblastoma multiforme; glomus tumors, multiple; hepatoblastoma; hepatocellular cancer; hepatocellular carcinoma; leukemia, acute lymphoblastic; leukemia, acute myeloid; leukemia, acute myeloid, with eosinophilia; leukemia, acute nonlymphocytic; leukemia, chronic myeloid; Li-Fraumeni syndrome; liposarcoma, lung cancer; lung cancer, small cell; lymphoma, non-Hodgkin's; lynch cancer family syndrome II; male germ cell tumor; mast cell leukemia; medullary thyroid; medulloblastoma; melanoma, malignant melanoma, meningioma; multiple endocrine neoplasia; multiple myeloma, myeloid malignancy, predisposition to; myxosarcoma, neuroblastoma; osteosarcoma; osteocarcinoma, ovarian cancer; ovarian cancer, serous; ovarian carcinoma; ovarian sex cord tumors; pancreatic cancer; pancreatic endocrine tumors; paraganglioma, familial nonchromaffin; pilomatricoma; pituitary tumor, invasive; prostate adenocarcinoma; prostate cancer; renal cell carcinoma, papillary, familial and sporadic; retinoblastoma; rhabdoid predisposition syndrome, familial; rhabdoid tumors; rhabdomyosarcoma; small-cell cancer of lung; soft tissue sarcoma, squamous cell carcinoma, basal cell carcinoma, head and neck; T-cell acute lymphoblastic leukemia; Turcot syndrome with glioblastoma; tylosis with esophageal cancer; uterine cervix carcinoma, Wilms' tumor, type 2; and Wilms' tumor, type 1, and the like.

According to a specific embodiment, the cancer is breast cancer or ovarian cancer.

The formation of new blood vessels, angiogenesis, is critical for the progression of many diseases, including cancer metastases, diabetic retinopathy, and rheumatoid arthritis. Many factors associated with angiogenesis, e.g., cell adhesion molecules, cytokines, and growth factors, are regulated through the proteasome, and, hence, alteration of its activity will affect the degree of vessel formation. Oikawa et al [Biochem Biophys Res Commun. 1998; 246:243-248] demonstrated that a particular proteasome inhibitor, lactacystin significantly reduced angiogenesis, suggesting that it, or related compounds, could be beneficial in disease states that rely on the formation of new blood vessels.

Thus, according to another embodiment, the disease associated with aberrant protein degradation is an angiogenesis associated disease.

The proteasome is intimately linked to the production of the majority of the class I antigens. It is therefore conceivable that CSN regulators might also increase the chance of viral infections such as HIV.

Through its regulation of NF-kappa B, the proteasome is central to the processing of many pro-inflammatory signals. Once released from its inhibitory complex through proteasome degradation of I kappa B, NF-kappa B induces the activation of numerous cytokines and cell adhesion molecules that orchestrate the inflammatory response. Thus, the present invention contemplates use of the COP9 signalosome regulators of the present invention for the treatment of inflammatory diseases including but not limited to asthma, ischemia and reperfusion injury, multiple sclerosis, rheumatoid arthritis, psoriasis, autoimmune thyroid disease, cachexia, Crohn disease, hepatitis B, inflammatory bowel disease, sepsis, systemic lupus erythematosus, transplantation rejection and related immunology and autoimmune encephalomyelitis.

In addition, it has been shown that blocking proteasome activity reduces neuron and astrocyte degeneration and neutrophil infiltration and therefore can be potential therapy for stroke and neurodegenerative diseases including Parkinson's disease, Alzheimer disease, and amyotrophic lateral sclerosis (ALS). Thus, the present invention considers using COP9 signalosome regulators for the treatment of these diseases as well.

The agents of the present invention may be provided per se or as part of a pharmaceutical composition, where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the agents which reduce the amount of CSNAP from being incorporated into the CSN, accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations, which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions that can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (proteasome inhibitor) effective to prevent, alleviate or ameliorate symptoms of a disorder (e.g., cancer) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer, as further detailed below. Such information can be used to more accurately determine useful doses in humans.

Toxicity and therapeutic efficacy of the active ingredients described herein can be determined by standard pharmaceutical procedures in vitro, in cell cultures or experimental animals, as further detailed below. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to ensure blood or tissue levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

As mentioned, various animal models may be used to test the efficacy of the agent of the present invention. A transgenic mouse model for cancer (e.g., breast cancer) such as the erb model (Shah N., et al., 1999, Cancer Lett. 146: 15-2; Weistein E J., et al., 2000, Mol. Med. 6: 4-16) or MTV/myc model (Stewart T A et al., 1984, Cell, 38: 627-637), the c-myc model (Leder A., et al., 1986, Cell, 45:485-495), v-Ha-ras or c-neu model (Elson A and Leder P, 1995, J. Biol. Chem. 270: 26116-22) can be used to test the ability of the agents of the present invention to suppress tumor growth in vivo.

For the formation of solid tumors, athymic mice can be injected with human or animal (e.g., mouse) cancerous cells such as those derived from breast cancer, ovarian cancer, prostate cancer or thyroid cancer, and following the formation of cancerous tumors the mice can be subjected to intra-tumor and/or systemic administration of an agent capable of reducing the amount of CSNAP from binding to the CSN.

The following cell lines (provided with their ATCC Accession numbers) can be used for each type of cancer model:

For Breast Cancer:
Human Breast Cancer Cell Lines—
MDA-MB-453 (ATCC No. HTB-131), MDA-MB-231 (ATCC No. HTB-26), BT474 (ATCC No. HTB-20), MCF-7 (ATCC No. HTB-22), MDA-MB-468.

For Ovarian Cancer:
Human Ovarian Cancer Cell Lines—
SKOV3 (ATCC No. HTB-77), OVCAR-3 HTB-161), OVCAR-4, OVCAR-5, OVCAR-8 and IGROV1;

For Prostate Cancer:
Human Prostate Cancer Cell Lines—
DU-145 (ATCC No. HTB-81), PC-3 (ATCC No. CRL-1435);

For Thyroid Cancer:
Human Derived Thyroid Cancer Cell Lines—
FTC-133, K1, K2, NPA87, K5, WR082-1, AR089-1, DR081-1;

For Lung Cancer:
Mouse Lung Carcinoma LL/2 (LLCI) Cells (Lewis Lung Carcinoma)—

These cells are derived from a mouse bearing a tumor resulting from an implantation of primary Lewis lung carcinoma. The cells are tumorigenic in C57BL mice, express H-2b antigen and are widely used as a model for metastasis and for studying the mechanisms of cancer chemotherapeutic agents (Bertram J S, et al., 1980, Cancer Lett. 11: 63-73; Sharma S, et al. 1999, J. Immunol. 163: 5020-5028).

For Melanoma:
Mouse B16-F10 Cells (Melanoma)—
The cells are derived from mouse (C57BL/6J) bearing melanoma (Briles E B, et al., 1978, J. Natl. Cancer Inst. 60: 1217-1222).

The cancerous cells can be cultured in a tissue culture medium such as the DMEM with 4 mM L-glutamine adjusted to contain 1.5 g/L sodium bicarbonate and 4.5 g/L glucose, supplemented with 10% fetal calf serum (FCS), according to known procedures (e.g., as described in the ATCC protocols).

Tumor Formation in Animal Models by Administration of Cancerous Cells—

Athymic nu/nu mice (e.g., female mice) can be purchased from the Jackson Laboratory (Bar Harbor, Me.). Tumors can be formed by subcutaneous (s.c.) injection of cancerous cells (e.g., $2\times10^6$ cells in 100 µl of PBS per mouse). Tumors are then allowed to grow in vivo for several days (e.g., 6-14 days) until they reach a detectable size of about 0.5 cm in diameter. It will be appreciated that injection of cancerous cells to an animal model can be at the organ from which the cell line is derived (e.g., mammary tissue for breast cancer, ovary for ovarian cancer) or can be injected at an irrelevant tissue such as the rear leg of the mouse.

To test the effect of the agents of the present invention on inhibition of tumor growth, the agents may be administered to the animal model bearing the tumor either locally at the site of tumor or systemically, by intravenous injection of infusion, via, e.g., the tail vein. The time of administration may vary from immediately following injection of the cancerous cell line (e.g., by systemic administration) or at predetermined time periods following the appearance of the solid tumor (e.g., to the site of tumor formation, every 3 days for 3-10 times as described in Ugen K E et al., Cancer Gene Ther. 2006 Jun. 9; [Epub ahead of print]).

Administration may be effected using a nucleic acid construct designed to express the active agent (e.g., a viral vector), naked pDNA and/or liposomes, as follows.

Tumor sizes are measured two to three times a week. Tumor volumes are calculated using the length and width of the tumor (in millimeters). The effect of the treatment can be evaluated by comparing the tumor volume using statistical analyses such as Student's t test. In addition, histological analyses can be performed using markers typical for each type of cancer.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein, the term "preventing" refers to keeping a disease, disorder or condition from occurring in a subject who may be at risk for the disease, but has not yet been diagnosed as having the disease.

As used herein, the term "subject" includes mammals, preferably human beings at any age which suffer from the pathology. Preferably, this term encompasses individuals who are at risk to develop the pathology.

It will be appreciated that since prevention of CSNAP from binding to the COP9 signalosome was shown to prevent cell cycle progression and induce cell death, the present inventors also contemplate a method for screening for agents which are useful for treating a disease associated with aberrant protein degradation. The method comprises:

(a) introducing the agent into a cell;

(b) analyzing the amount of CSNAP that is incorporated into the CSN of the cell, wherein a reduction in the amount of CSNAP that is incorporated into the CSN following step (a) is indicative that the agent is useful for treating condition associated with aberrant protein degradation.

The CSN complex may be in an isolated form or may be inside a cell population. According to one embodiment, the cells of the cell population are viable. According to another embodiment, the CSN complex is located inside a protein extract.

It will be appreciated that the amount of CSNAP which is incorporated into the CSN complex may be analyzed on the protein level using method known in the art including but not limited to immunoprecipitation assays, Western blot, radioimmunoassay, enzyme linked immunosorbent assay, FACs analysis and immunohistochemical analysis. The amount or activity of PSMD1 may be analyzed on the polynucleotide level using method known in the art including but not limited to Northern blot analysis, RT-PCR and microarray chips.

The candidate agents that may be tested as potential regulators of the CSN according to the method of the present invention include, but are not limited to, nucleic acids, e.g., polynucleotides, ribozymes, siRNA and antisense molecules (including without limitation RNA, DNA, RNA/DNA hybrids, peptide nucleic acids, and polynucleotide analogs having altered backbone and/or bass structures or other chemical modifications); proteins, polypeptides (e.g. peptides), carbohydrates, lipids and "small molecule" drug candidates. "Small molecules" can be, for example, naturally occurring compounds (e.g., compounds derived from plant extracts, microbial broths, and the like) or synthetic organic or organometallic compounds having molecular weights of less than about 10,000 Daltons, preferably less than about 5,000 Daltons, and most preferably less than about 1,500 Daltons.

Following identification of a suitable agent it may be tested using additional assays such as the ones described herein above. Once therapeutic activity is confirmed, the agent may be synthesized in larger amounts for further testing and formulation.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Cell Culturing, Transfections and UVC Exposure:

HAP1 WT and ΔCSNAP CRISPR cell lines was purchased from Haplogene GmbH, Austria, and were cultured in humidified CO2 incubator at 37° C. in Iscove's Modified Dulbecco's medium (IMDM) supplemented with 10% fetal calf serum, penicillin-streptomycin and Mycozap (Lonza). HAP1 cells were transfected with phyg-CSNAP-Cerulean, phyg-ΔN-CSNAP-Cerulean, phyg-FBXL15-FLAG using JetPrime reagent (Polyplus). Cerulean expressing cell lines were isolated and sorted for low-medium expression levels by fluorescence-activated cell sorting (FACSAria Fusion; BD Biosciences) and expanded in complete IMDM. HEK293 cells were obtained from Eitan Reuveny (Weizmann Institute of Science), and were cultivated in Dulbecco's modified Eagle's medium (DMEM) supplemented with 10% fetal calf serum, penicillin-streptomycin, sodium pyruvate, nonessential amino acids (Biological Industries), and MycoZap (Lonza). For UV treatment, plates were washed twice with PBS and after removal of the liquid were illuminated with 20 J/m$^2$ UV-C light.

Confocal Microscopy:

Confocal imaging of WT, ΔCSNAP and ΔCSNAP cells expressing CSNAP-Cerulean was performed at 60× magnification as previously described (Rozen et al., 2015). Cell area was measured by Olympus Fluoview software. The area of at least 27 cells and nuclei were measured, and plotted as boxes extending from the third (Q3) to the first quartiles (Q1). Whiskers at the top and bottom represent measurements above the Q3 or below the Q1, respectively.

Immunoprecipitaions:

For immunoprecipitation HEK293 or HAP1 cells were lysed in 50 mM Tris pH 7.4, 150 mM NaCl, 0.5% NP40, 5 mM Na-o-vanadate, 4 mM Na-pyrophosphate and I3-glycerophosphate and protease inhibitors, and 1 mg total protein was incubated with 10 μl anti-CSN3 (Abcam ab79398) or 35 μl anti-FLAG resin (Sigma A2220) overnight, and when free antibody was used with 35 μl protein G sepharose slurry for 1 hour. Bound proteins were eluted with 2× Laemmli sample buffer.

Western Blots:

Proteins were separated on 12% SDS-PAGE and transferred to PVDF membranes. Primary antibodies used for detection: anti-CSN1 (Enzo PW8285), anti-CSN2 (Abcam ab10462), anti-CSN3 (ab79398), anti-CSN5 (ab495), anti-CSN6 (PW 8295), anti-CSN8 (BML-PW8290), anti-PDCD4 (ab80590), anti-Cullin1 (ab75817), anti-Cullin2 (ab166917), anti-Cullin3 (ab75851), anti-Cullin4AB (ab76470), anti-Cullin5 (ab184177), anti-DDB2 (ab51017), anti-PARP1 (Santa Cruz sc-8007), anti-FLAG (Sigma F3165), anti-pChk1 (Cell signaling 2341), anti-pChk2 (Millipore 04-1092), anti-GAPDH (Millipore MAB374).

Comet Assay:

Alkaline single cell electrophoresis was performed according to the protocol from Trevigen. HAP1 cells were treated with 20 J/m$^2$ UV-C light and 6 hours post-exposure cells were trypsinized, counted, and suspended in ice-cold PBS (—Ca/—Mg) to 2×10$^5$ cells/ml. Fifty μl of cell suspension was mixed with 450 μl LM-agarose (Trevigen) and 50 μl was pipetted onto the comet slide, and incubated in dark at 4° C. for 30 minutes. Slides were immersed into lysis solution (Trevigen) for 1 hour at 4° C. then equilibrated to alkaline electrophoresis solution (300 mM NaOH, 2 mM EDTA, pH>13) for 20 minutes at room temperature, run at 1 V/cm (~300 mA constant) in ice-cold alkaline electrophoresis solution for 30 minutes. Then slides were neutralized for 5 minutes in 400 mM Tris pH7.5, rinsed in distilled water, immersed into 70% ethanol for 5 minutes and dried at room temperature. DNA was stained with SYBR Gold (Invitrogen) and the slides were dried completely before imaging. Images were acquired using an inverted Nikon microscope (Eclipse Ti, Nikon, Japan) with 20× objective and with cooled electron-multiplying charge-coupled device camera (iXon Ultra, Andor, Ireland). Comet parameters were analyzed using CASP comet software for minimum 74 ells per sample in 3 biological samples, in duplicates.

Colony Forming Assay:

Untreated or 20 J/m$^2$ UV-C exposed WT and ΔCSNAP cells were trypsinized, counted, and 100 untreated or 5000 UV-illuminated cells were plated per each 10 cm tissue culture dish in triplicates, and were incubated in normal growth conditions for 8 days in triplicates. The plates were washed twice with PBS, dried, stained with 0.15% Crystal violet in methanol for 3 minutes. Stained plates were rinsed with tap water and air dried before scanning. Colony counts were measured using OpenCFU software.

SILAC:

HAP1 cells were grown in SILAC IMDM (Invitrogen) with 10% dialyzed fetal calf serum (Biological Industries, 04-011-1A) supplemented with 25 µg/ml light L-lysine and L-arginine (13C6, 15N4) (Cambridge Isotopes) for WT cells, and heavy L-lysine and L-arginine for ΔCSNAP cells. Cells were incubated with 5 µM MG132 for 4 hours before harvesting. Briefly, the samples were lysed using 8M urea, mixed at 1:1 protein: protein ration and digested with trypsin, followed by a desalting step. The resulting peptides were fractionated offline using high pH reversed phase chromatography, followed by enrichment for k-e-GlyGly using the Cell Signaling PTMScan™ Ubiquitin Remnant Motif (K-ε-GG) kit #5562 (antibody based). Each fraction was then analyzed using online nanoflow liquid chromatography (nanoAcquity) coupled to high resolution, high mass accuracy mass spectrometry (Fusion Lumos). Raw data was processed with MaxQuant v1.5.5.1. The data was searched with the Andromeda search engine against the human proteome database appended with common lab protein contaminants and allowing for GG modifications of lysines. The ratio of H/L (heavy to light) was calculated, and were log transformed.

Label Free Quantitation:

WT and ΔCSNAP cells were lysed in 50 mM Tris pH 7.4, 150 mM NaCl, 0.5% NP40, 5 mM Na-o-vanadate, 4 mM Na-pyrophosphate and β-glycerophosphate, and 1 mg total protein was used for immunoprecipitation using anti-CSN3 antibody (ab79698) as above in 3 biological replicates, and proteins were eluted by 75 µl of 0.1M glycine-HCl pH2.5. The beads were washed in TBS and were subjected to on-bead tryptic digestion8 M urea in 0.1 M Tris, pH 7.9 was added onto TBS washed beads and incubated for 15 min in room temperature. Proteins were reduced by incubation with dithiothreitol (5 mM; Sigma) for 60 min at room temperature, and alkylated with 10 mM iodoacetamide (Sigma) in the dark for 30 min at room temperature. Urea was diluted to 2 M with 50 mM ammonium bicarbonate. 250 ng trypsin (Promega; Madison, Wis., USA) was added and incubated overnight at 37° C. followed by addition of 100 ng trypsin for 4 hr at 37° C. Digestions were stopped by addition of trifluroacetic acid (1% final concentration). Following digestion, peptides were desalted using Oasis HLB µElution format (Waters, Milford, Mass., USA), vacuum dried and stored in −80° C. until further analysis. ULC/MS grade solvents were used for all chromatographic steps. Each sample was loaded using split-less nano-Ultra Performance Liquid Chromatography (10 kpsi nanoAcquity; Waters, Milford, Mass., USA). The mobile phase was: A) H2O+0.1% formic acid and B) acetonitrile+0.1% formic acid. Desalting of the samples was performed online using a reversed-phase Symmetry C18 trapping column (180 µm internal diameter, 20 mm length, 5 µm particle size; Waters). The peptides were then separated using a T3 HSS nano-column (75 µm internal diameter, 250 mm length, 1.8 µm particle size; Waters) at 0.35 µL/min. Peptides were eluted from the column into the mass spectrometer using the following gradient: 4% to 30% B in 55 min, 30% to 90% B in 5 min, maintained at 90% for 5 min and then back to initial conditions. The nanoUPLC was coupled online through a nanoESI emitter (10 µm tip; New Objective; Woburn, Mass., USA) to a quadrupole orbitrap mass spectrometer (Q Exactive Plus, Thermo Scientific) using a FlexIon nanospray apparatus (Proxeon). Data was acquired in data dependent acquisition (DDA) mode, using a Top20 method. MS1 resolution was set to 70,000 (at 400 m/z), mass range of 300-1650 m/z, AGC of 3e6 and maximum injection time was set to 20 msec. MS2 resolution was set to 17,500, quadrupole isolation 1.7 m/z, AGC of 1e6, dynamic exclusion of 30 sec and maximum injection time of 60 msec. Raw data was imported into the Expressionist® software version 9.1.3 (Genedata) and processed as described here. The software was used for retention time alignment and peak detection of precursor peptides. A master peak list was generated from all MS/MS events and sent for database searching using Mascot v2.5.1 (Matrix Sciences). Data was searched against the human sequences UniprotKB (www (dot)uniprot(dot)org/) appended with the mutant MYEOV sequences and common laboratory contaminant proteins. Fixed modification was set to carbamidomethylation of cysteines and variable modifications were set to oxidation of methionines and deamidation of N or Q. Search results were then filtered using the PeptideProphet algorithm to achieve maximum false discovery rate of 1% at the protein level. Peptide identifications were imported back to Expressionist to annotate identified peaks. Quantification of proteins from the peptide data was performed using an in-house script. Data was normalized base on the total ion current. Protein abundance was obtained by summing the three most intense, unique peptides per protein. A Student's t-Test, after logarithmic transformation, was used to identify significant differences across the biological replica. Fold changes were calculated based on the ratio of arithmetic means of the case versus control samples.

Total Proteome Analysis and Bioinformatics:

WT and ΔCSNAP cells were lysed in SDT buffer (4% SDS, 100 mM Tris/HCl pH 7.6, 0.1 M dithiothreitol) and subjected to a tryptic digestion using FASP™ Protein Digestion Kit (Expedeon). The resulting peptides were desalted and analyzed on the LC-MS instrument (Q-Exactive plus) in DDA mode with an inclusion list of your 87 selected proteins. The raw data was processed in Expressionist by Genedata that used Mascot as the search engine against the uniprot human proteome database appended with your mutant sequences and common protein contaminants. The identifications were filtered to a maximum of 1% FDR on both peptide and protein levels. Protein inference was done by an in-house script. Overall about 4000 proteins were identified and quantified. Proteomics data, after logarithmic transformation and flooring, were analyzed by two-way ANOVA using the 2 factors: strain and UV treatment, as well as their interaction. Proteins with P-value below 0.05 and an absolute fold change above 1.5 were considered as being differentially expressed. The proteins were filtered to keep proteins that had an absolute fold change of at least 1.5 and p-value below 0.05 at least in one of the following pair-wise comparisons: 1. WT UV/WT untreated, 2. ΔCSNAP UV/ΔCSNAP untreated, 3. ΔCSNAP untreated/WT untreated, 4. ΔCSNAP UV/WT UV. The log 2 intensities of the 347 proteins passed these criteria (the ANOVA analysis with all samples, after flooring was used) were clustered using the k-means algorithm with Pearson dissimilarity as distance measure to 4 or 5 clusters. The log 2 intensities were standardized to have for each protein zero mean and unit standard deviation. The proteins in each cluster can be obtained by filtering the excel file.

Cell Cycle Analysis:

Cells were synchronized to G1/S phase using double thymidine block as described in (Füzesi-Levi et al., 2014). UV treated cells were exposed to 5 J/m$^2$ dose at release, and fixed with ethanol at different time points. Cell cycle phases were assessed by flow cytometry (LSRII, BD Biosciences) following propidium iodide staining. Asynchronous cells were analyzed using propidium iodide and BrdU double staining. $10^5$ cells were denatured after fixation using 2N HCl, 0.5% Triton X-100 in PBS for 30 minutes, neutralized in 0.1M Na2B4O7 pH8.5 and incubated with 5 µl of anti-BrdU-FITC (eBioscience 11-5071-41) 1% BSA, 0.5% Triton X-100 in PBS for 1 hour. Cells were washed in 1% BSA in PBS and resuspended in PBS containing 50 µg/ml propidium iodide and 50 µg/ml RNAse A, and analyzed in FACSAria Fusion flow cytometer (BD Biosciences).

Resazurin Assay:

WT, ΔCSNAP, ΔCSNAP-Cerulean and ΔCSNAP-ΔC-Cerulean expressing cells were trypsinized, counted, and 5000 cells/well in 12 well plate were seeded in 4 replicates. Cells in one plate were seeded directly to 30 µg/mlresazurin containing growth medium and fluourescence intensity was measured (540/600 nm) after 2 hours, for initial proliferation value. The other plates were either UV-exposed at 20 J/m$^2$ 24 hours after seeding or left untreated. Two or 4 hours post-UV the growth medium was changed to 30 µg/ml resazurin containing medium and incubated for 2 hours, and fluorescence was measured. Proliferation was calculated at each time point normalizing to the initial proliferation value.

Measurement of Viable and Dead Cell Populations:

Determination of percentage of live, early apoptotic and late apoptotic/necrotic cells in WT and ΔCSNAP cultures was performed using Annexin V-FITC Apoptosis Detection Kit (APOAF-20TST, Sigma) by flow cytometry. Single cells were analyzed for AnnexinV-FITC and propidium iodide fluorescence, and early apoptotic cells (annexin V positive, PI negative), late apoptotic/necrotic cells (annexin V positive, PI positive), and viable cells (annexin V negative, PI negative) were gated and quantified.

Example 1

The Lack of CSNAP Gives Rise to Phenotypic Effects

Figure 1B:
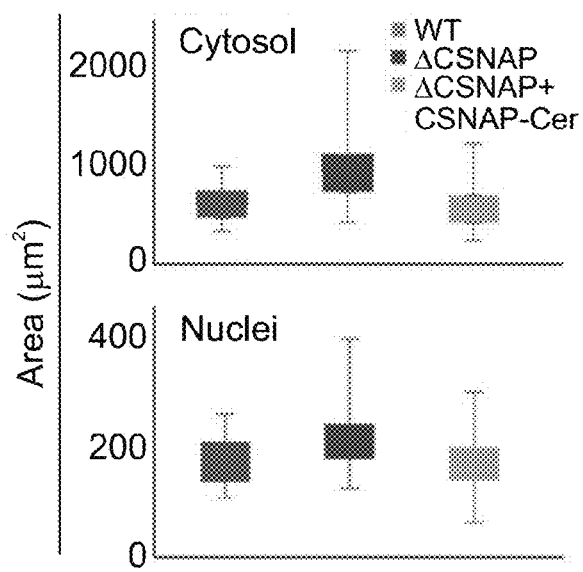
Figure 1C:
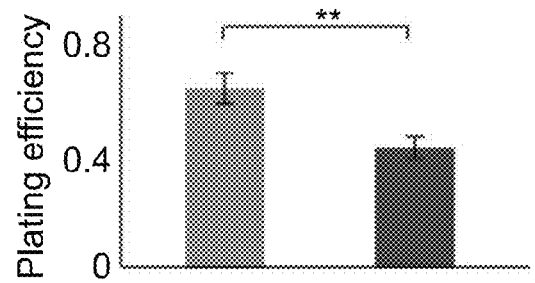
Figure 1D:
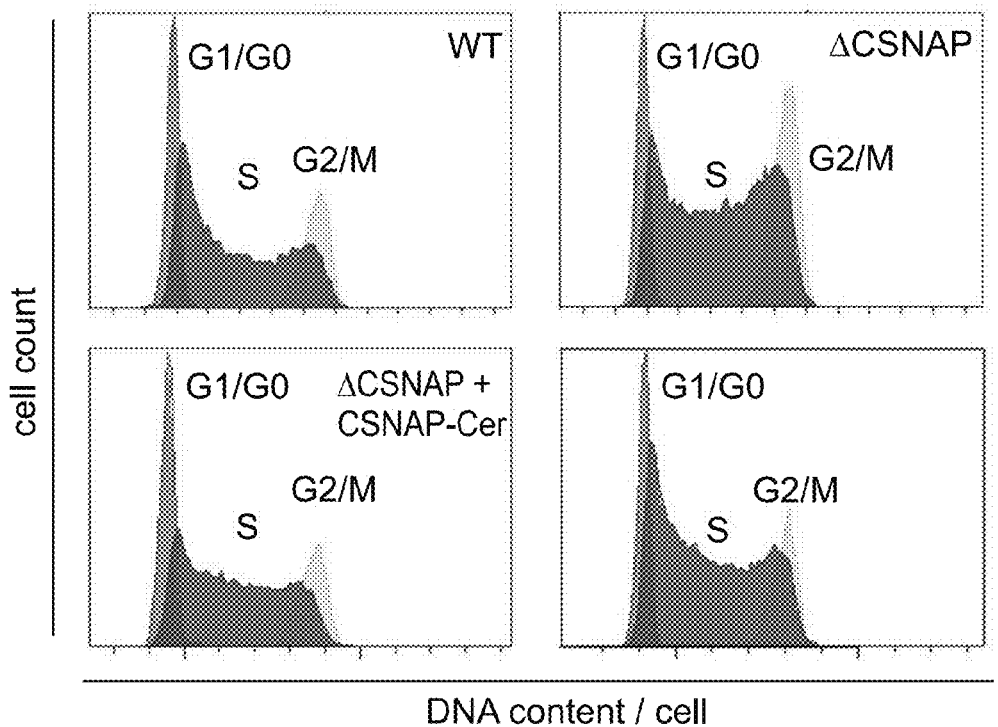
Figure 1E:
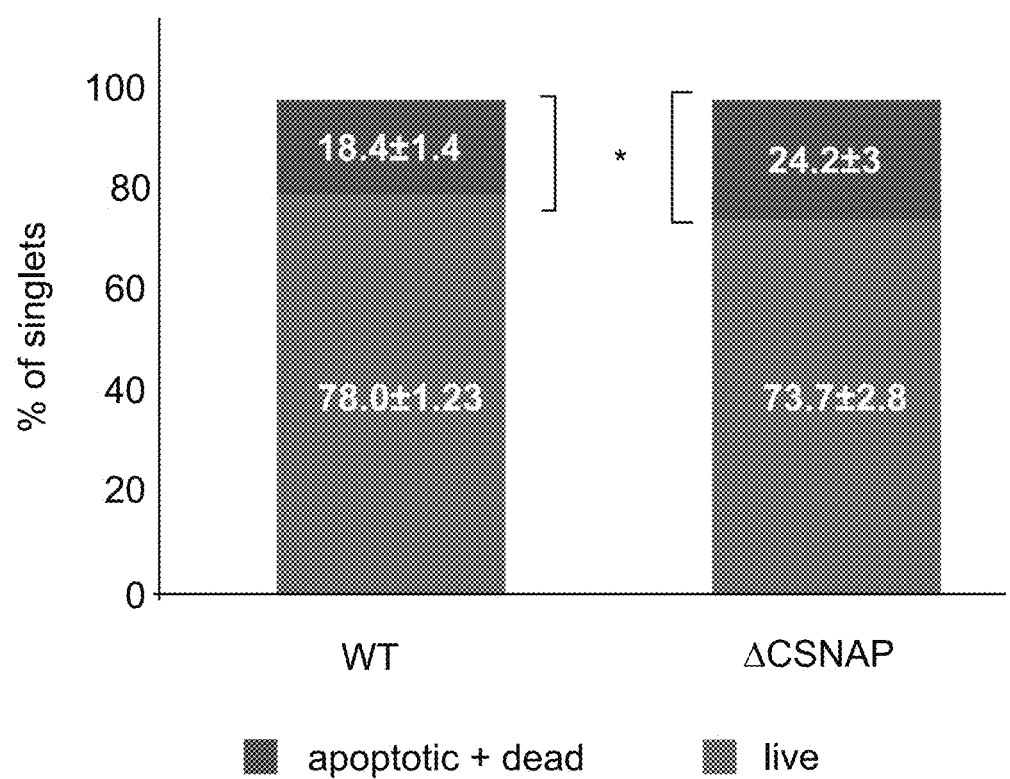

To investigate the functional significance of CSNAP, HAP-1 cell lines lacking CSNAP (ΔCSNAP cells) were used. These cells exhibit enlarged and flattened morphology in comparison to wild-type (WT) cells (Rozen et al, Cell Rep 13, pages 585-598, 2015). This phenotype can be rescued by introducing CSNAP-cerulean into ΔCSNAP cells (FIGS. 1A and 1B). The reproductive ability of the ΔCSNAP cells was assessed by performing colony formation assays. Cells lacking CSNAP were found to have a significantly lower potential to form colonies in comparison to WT cells (FIG. 1C). Next, the effect of CSNAP on cell cycle distribution was investigated. Flow cytometry analysis indicated that compared to WT cells, ΔCSNAP cells display a larger S and G2 phase population (FIG. 1D). This phenotype can be prevented by exogenous expression of CSNAP-cerulean, but not by the truncated form of the protein, which is lacking the C-terminal region (ΔC-CSNAP-Cerulean, truncated CSNAP-MKPAVDEMFPEGAGPYVDLDEAGGSTGLL-MDLAANEKAVHA; SEQ ID NO: 6) that is crucial for integration into the CSN. Hence, CSNAP function within the CSN complex is necessary for proper cell cycle progression. Cells lacking CSNAP cell harbor larger population of dead cells (FIG. 1E). Overall, the results indicate that the lack of CSNAP yields a cellular phenotype characterized by altered cell morphology, reproductive capacity, viability and cell cycle phase distribution.

Example 2

CSNAP is Required for DNA Repair

Figure 2A:
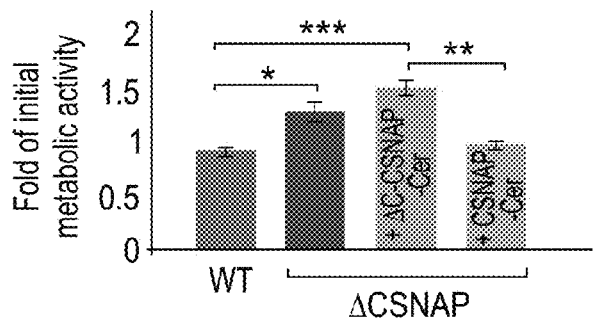

Since the CSN complex has been demonstrated to be a crucial player in the DNA damage response, the present inventors explored whether CSNAP is required for this activity. Initially, they measured cell proliferation prior to and following the induction of DNA damage by UV-C irradiation (FIG. 2A). As expected, WT cells exhibited reduced cellular proliferation in order to enable DNA damage repair. This arrest, however, was not detected in cells lacking CSNAP, nor in cells exogenously expressing ΔC-CSNAP-Cerulean, which is not incorporated into the CSN complex. Nevertheless, rescue was achieved by over-expressing the full length CSNAP protein that is part of the CSN complex.

Figure 2C:
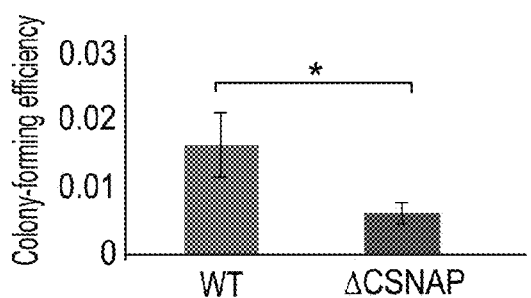
Figure 2B:
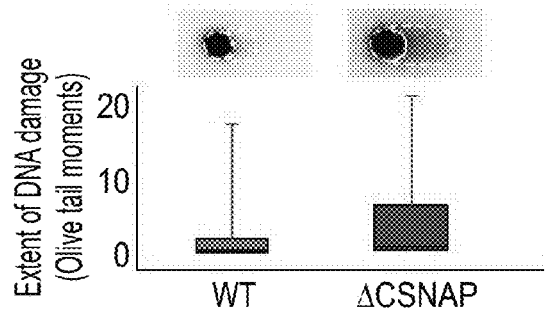

Comet assay analysis that measures the repair capacity following DNA damage, indicated that ΔCSNAP cells have a longer tail moment, which is associated with the accumulation of both single and double strand DNA breaks. Similarly, comparison of the colony forming potential of WT and ΔCSNAP cells following UV irradiation indicated a significant reduction of 2.7 fold in the number of colonies of cells lacking CSNAP (FIG. 2C). This finding suggests that the accumulation of damaged DNA compromises the cells reproductive ability.

Figure 2E:
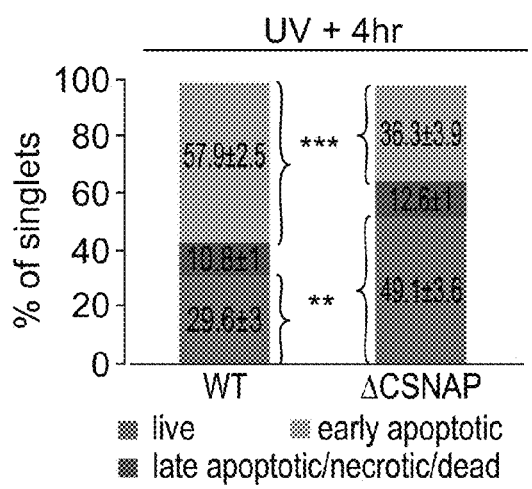
Figure 2D:
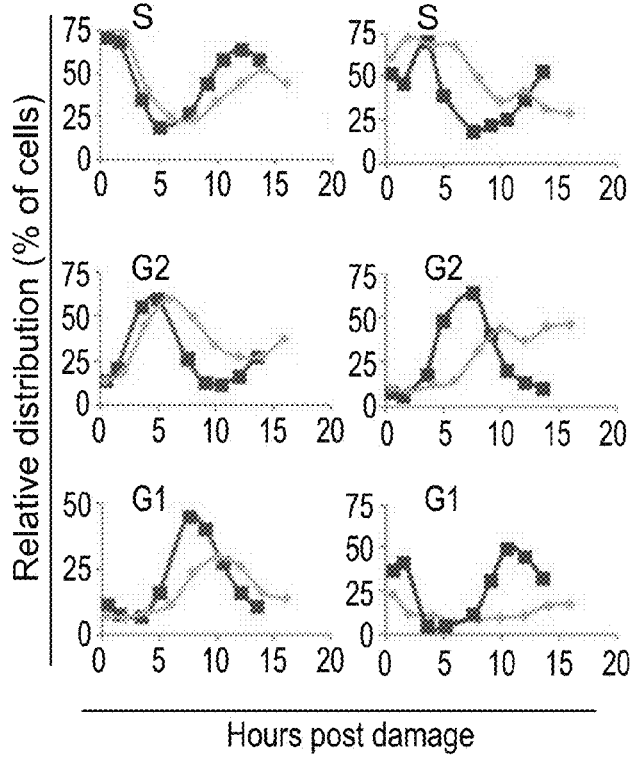

Considering that an increase in the extent of DNA damage induces cell cycle arrest, the cell cycle distribution of WT and ΔCSNAP cells exposed to UV irradiation following a double thymidine block was evaluated. After the release from cell cycle synchronization, ΔCSNAP cells proceeded from the G1/S block to the S phase significantly slower than WT cells, and reached the G2 phase with a delay of approximately 4 hours (FIG. 2D). However, following the induction of DNA damage, CSNAP depleted cells, unlike the WT cells that displayed a slight delayed progression, remained stalled in S and G2 phases. Considering that this scenario could be due to impaired checkpoint control and not exclusively due to a faulty DNA repair mechanism, the present inventors validated that the activation of Chk1 and Chk2 is not dependent on CSNAP (FIG. 7). Next, they determined whether the absence of CSNAP affects the cellular apoptotic processes.

To this end, they measured in WT and ΔCSNAP the populations of early apoptotic and late apoptotic cells in UV-exposed cultures 4 hours post damage using flow cytometry. The data indicated that following UV exposure, the population of the early apoptotic cell is significantly enlarged in WT cells, a phenomenon that does not occur in ΔCSNAP cells, suggesting that the latter fail to activate the early apoptotic response (FIG. 2E). Taken together, the results suggest that the assembly of CSNAP within the CSN is required for efficient activation of the DNA damage response.

Example 3

CSNAP Modulates the CSN Interacting Network

In order to define the role CSNAP serves within the CSN complex, the impact of CSNAP absence was assessed on both the enzymatic and non-enzymatic activities of the CSN ($CSN^{\Delta CSNAP}$ nomenclature is used herein to describe CSN complexes lacking CSNAP).

Figure 3A:
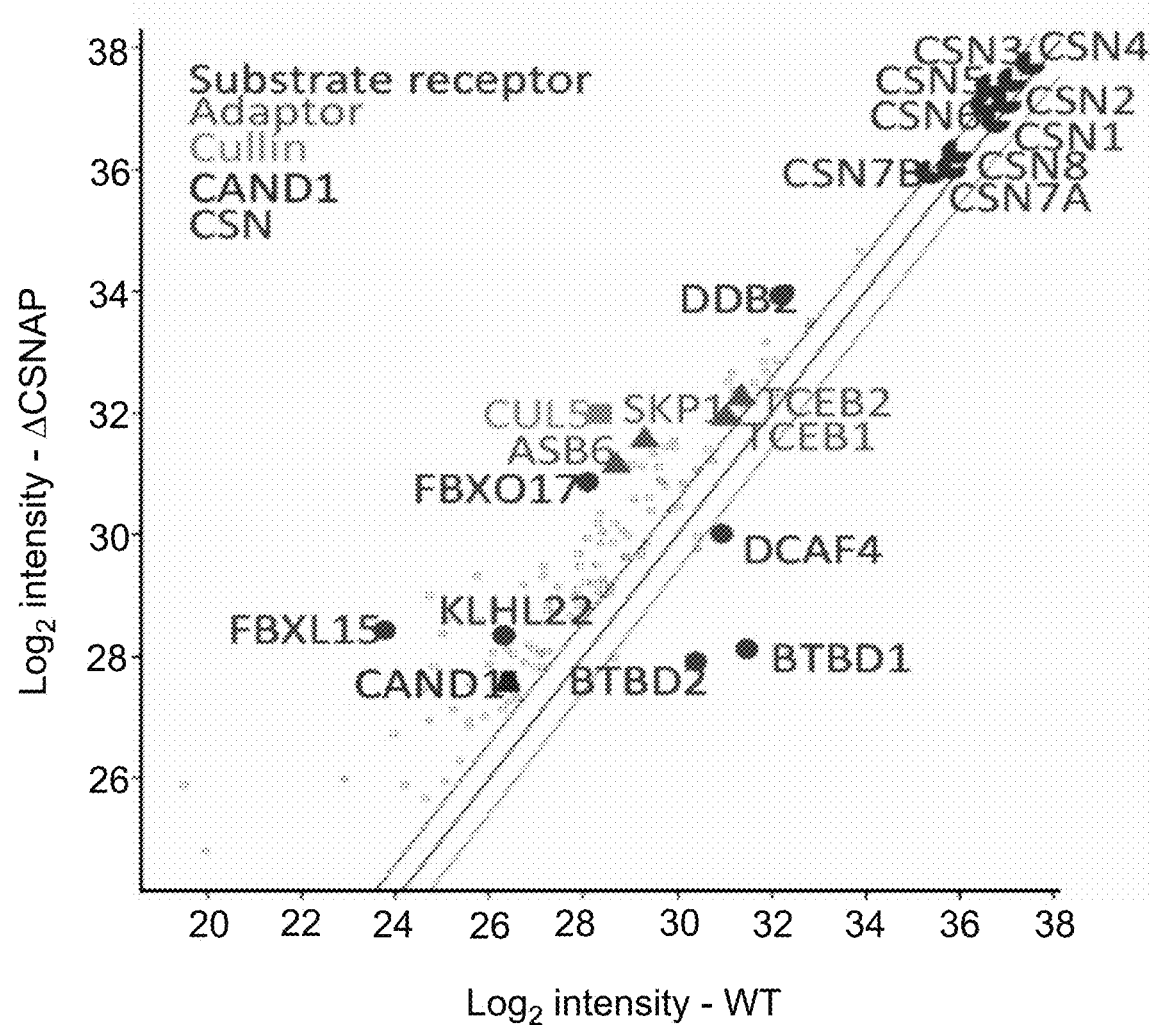

To examine whether the non-enzyamtic activity of $CSN^{\Delta CSNAP}$ is affected by the absence of CSNAP, label-free quantification of protein intensities from pull-down assays was performed coupled with mass spectrometry (MS) analysis of WT and ΔCSNAP cells using an anti-CSN3 antibody. The present inventors reasoned that if CSNAP affects CSN interaction with CRLs, differences in the array of protein binding partners will be revealed. Indeed, a large number of proteins that are significantly enriched in ΔCSNAP cells in comparison to WT were identified (FIG. 3A). Among them are mainly substrate receptors (DDB2, FBOX17, FBXL15 and KLH22) and adapters (TCEB2, TCEB1 and ASB6) CRL proteins. In the WT cells only three proteins were enriched DCAF4, BTBD2 and BTBD1 all of which are CRL substrate receptor proteins.

To validate these results, reciprocal co-immunoprecipitation experiments were carried out using anti-FLAG resin or an anti-CSN3 antibody. The results obtained for the ΔCSNAP and WT cell lines confirmed that FBXL15 and DDB2 binds tighter to the $CSN^{\Delta CSNAP}$ than to the WT complex (FIG. 3B). Notably, these results are not due to changes in the expression levels of CSN subunits as all CSN subunits (except CSNAP that was depleted from cells) appeared not to change significantly between the two cell lines (FIG. 3A), a finding that was further validated by Western blot analysis using antibodies against CSN subunits (FIGS. 3C and 3D). Similarly no changes in the expression levels or the neddylation state of the cullins was detected (FIG. 3C). Altogether, the data imply that changes in the cullin neddylation state may not account for the cellular characteristic of ΔCSNAP cells, but rather the manipulation of the CSN/CRL interaction strength is the cause of the knockout phenotype.

Example 4

CSNAP Affects the Interaction Between the CSN and CRL Complexes

Since it was found that $CSN^{\Delta CSNAP}$ binds differently to CRL components compared to CSN, the present inventors questioned whether such change in binding affects the exchange cycle, i.e., the repertoire of active CRLs and consequently the array of ubiquitinated proteins. To this end, large-scale analysis of protein ubiquitination was performed relying on the enrichment of ubiquitinated peptides after tryptic digestion by the K-ε-GG specific antibody for the di-glycyl remnant produced on ubiquitinated lysine residues. The relative difference in ubiquitination of WT and ΔCSNAP cells was quantified using the SILAC (stable isotope labeling by amino acids in cell culture) approach. Significant differences in the extent of ubiquitination in ΔCSNAP and WT cell lines were detected (FIG. 4). 162 ubiquitination sites, corresponding to 124, proteins were found to exist in WT and not in ΔCSNAP cells. Overall, the results indicate that CSNAP reduces the affinity between CSN and CRLs thereby affecting the CRL reconfiguration dynamics and consequently the repertoire of ubiquitinated proteins.

Example 5

The Absence of CSNAP Influences the Proteome

Considering the significant dependence of the ubiquitinated proteome on the presence of CSNAP, the present inventors wished to examine whether the impact of this subunit is also reflected in global proteome analysis. They therefore applied labeled free quantification of WT and ΔCSNAP cells before and after exposure to UV irradiation. Data were analyzed by two-way ANOVA taking into consideration both the UV treatment and the type of the cells (WT or ΔCSNAP). Proteins with an absolute fold change above 1.5 and p-value below 0.05 were considered as differentially expressed. According to the log intensities 347 up- or down-regulated proteins (in at least one of the pair-wise comparisons) were clustered into 5 clusters using the k-means algorithm with Pearson dissimilarity as measure of distance (FIG. 5A). Pathway analysis indicated the dominant cellular functions of each cluster.

One of the striking observations was that in contrast to the 150 proteins which displayed differential expression levels in WT cells, the expression of only 5 proteins was altered in response to DNA damage in ΔCSNAP (FIG. 5B). This results which reflect the inability of cells lacking CSNAP to reshape the proteome in response to DNA damage is in accordance with our finding that the DNA repair mechanism in ΔCSNAP cells is compromised (FIGS. 2A-E).

To validate the proteomics result, Western blot analysis was performed to monitor the expression levels of two proteins that displayed differential expression levels between WT and ΔCSNAP cells, i.e. PDCD4, a tumor suppressor that appears in cluster 4, and PARP1, a member of the PARP family, NQO1 and vimentin that appear in cluster 3 (FIG. 5A, see arrows on the right). As shown in FIG. 5C, Western blot analysis confirmed that unlike WT cell, PDCD4 is expressed at high levels in ΔCSNAP cells. The same is true for NQO1. Likewise, the blots validated that the expression of PARP1 in WT cells, is high under normal conditions and is decreased following UV induced DNA damage, while in ΔCSNAP cells, regardless of UV irradiation, low levels of PARP1 expression are maintained.

Beyond the difference in expression levels, it was noted that in WT cells, PARP1 is cleaved into smaller products (89 and 24 kDs) after UV-induced DNA damage, a phenomenon that was not observed in ΔCSNAP cells (FIG. 5C, D). The cleavage of PARP-1 by caspases is considered to be a hallmark of apoptosis. Therefore, the lack of PARP-1 cleavage in ΔCSNAP cells may explain the inability of these cells to activate the early apoptotic response, as seen in FIG. 2E.

Example 6

Competitive Peptides, which Block Binding of the CSNAP Protein into the Complex

The present inventors have devised a strategy is based on competition that will prevent the integration of the endogenous CSNAP into the complex, and as a result lead to ΔCSNAP phenotypic affects. This rational is based on the fact that the C-terminal region of CSNAP is essential for incorporation within the CSN complex (Rozen et al, Cell Reports, 2015). In addition, it was previously shown that CSNAP binds to two distinct structural elements of the complex, Csn3 and Csn5/6. Specifically, the C-terminal region of CSNAP, which is enriched with phenylalanine and aspartic acid residues, binds Csn3. Thus, the present inventors reasoned that by inserting a stabilized C-terminal CSNAP peptide into cells, which is lacking the N-terminal region, it will bind only the Csn3 site. This, in turn will prevent the incorporation of the endogenous CSNAP protein into the complex, leading to the cellular phenotypes that were observed in cells lacking CSNAP.

To validate this assumption, the present inventors fused the C-terminal segment of CSNAP (DFFNDFEDLFDDD-DIQ; SEQ ID NO: 1) to the N-terminal region of the fluorescent protein CeruleanΔΔC-CSNAP-Cerulean). Reciprocal co-immunoprecipitation experiments were performed using three lines of HAP-1 cells, WT cells, cells lacking CSNAP (ΔCSNAP cells) and WT cell stably expressing C-CSNAP-Cerulean. Immunoprecipitation analysis using an anti-GFP antibody validated that the C-CSNAP-Cerulean is integrated within the CSN (FIG. 8). As expected, cells harboring the C-CSNAP-Cerulean protein exhibited impaired progression of cell cycle as observed for ΔCSNAP cells (FIG. 9). These results emphasize that cells harboring a C-terminal peptide of CSNAP, leads to a similar phenotype as ΔCSNAP.

CONCLUSIONS

The examples show that CSNAP, the smallest CSN subunit, is critical for proper regulation of CRL activity and specificity. In particular, they demonstrate that the lack of CSNAP cause a range of cellular phenotypes as morphological growth defects, impaired DNA damage respond and hindered cell cycled progression. All these characteristics can be attributed to CSN malfunction. This conclusion is based on the finding that ΔCSNAP phenotypes could not be rescued by a form of the protein lacking the CSN integration sequence. Furthermore, the examples show that CSNAP reduces the affinity towards CRL complexes. Together these results imply that CSNAP significantly contributes to the non-enzymatic mechanism of CRL regulation.

Efficient dissociation from CRL assemblies is essential for reconfiguration of new CRL compositions in order to respond to changing regulatory inputs. Therefore, it is expected that the increased affinity of $CSN^{\Delta CSNAP}$ for CRLs will inhibit the dynamic CRL exchange cycle and reduce cellular adaptation to stimuli (FIG. 6). This is exactly what was observed following UV irradiation of ΔCSNAP cells: proteome reshaping (FIGS. 5A-C) and repair of damaged DNA (FIGS. 2A-E) were compromised. The data also indicated that the impact of CSN/CRL partitioning extends beyond CRL substrates to the entire proteome (FIG. 4). Altogether, these findings reflect the prominence of the non-enzymatic CRL-inhibitory activity of CSN.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of treating cancer, comprising administering to a subject in need thereof a therapeutically effective amount of a peptide comprising the sequence as set forth in SEQ ID NO: 1 wherein the peptide is no longer than 30 amino acids, wherein said amino acid sequence is comprised in the C-terminus of CSNAP, thereby treating the cancer.

* * * * *